Figure 1A:
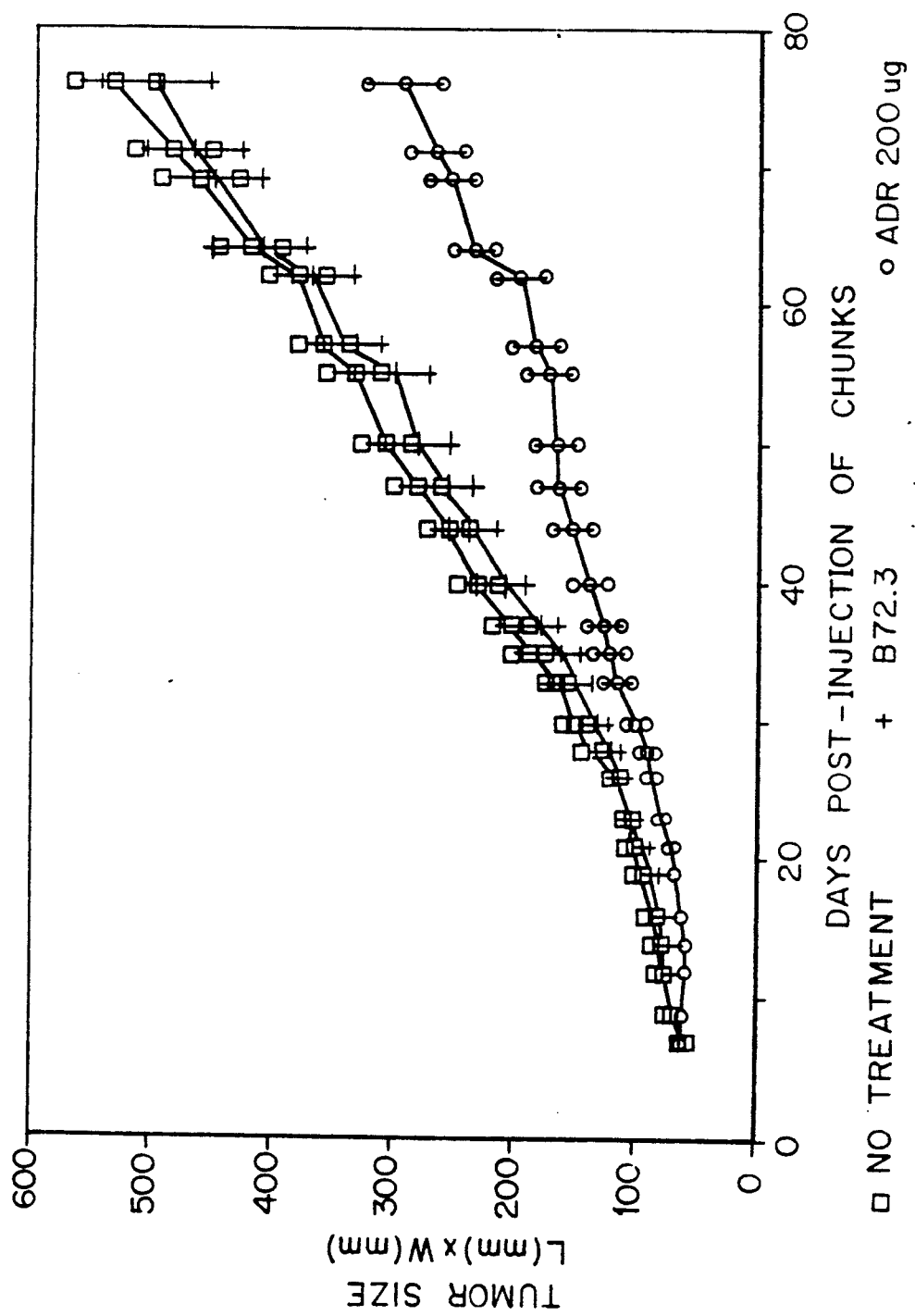

United States Patent [19]

King et al.

[11] Patent Number: 5,162,512

[45] Date of Patent: *Nov. 10, 1992

[54] AMINE DERIVATIVES OF ANTHRACYCLINE ANTIBODIES

[75] Inventors: H. Dalton King, Yardley, Pa.; Anthony D. Lopes, Hopewell; Robert D. Radcliffe, Titusville, both of N.J.; John D. Rodwell, Yardley, Pa.; Daniel J. Coughlin, Robbinsville, N.J.

[73] Assignee: Cytogen Corporation, Princeton, N.J.

[*] Notice: The portion of the term of this patent subsequent to Aug. 21, 2007, has been disclaimed.

[21] Appl. No.: 199,549

[22] Filed: May 27, 1988

Related U.S. Application Data

[63] Continuation-in-part of Ser. No. 58,440, Jun. 5, 1987, Pat. No. 4,950,738, which is a continuation-in-part of Ser. No. 650,375, Sep. 13, 1984, Pat. No. 4,867,973, which is a continuation-in-part of Ser. No. 650,754, Sep. 13, 1984, abandoned, which is a continuation-in-part of Ser. No. 356,315, Mar. 9, 1982, Pat. No. 4,671,958.

[51] Int. Cl.⁵ .................................... C07H 15/24
[52] U.S. Cl. .................................. 536/6.4; 530/322
[58] Field of Search ................. 530/322; 536/6.4; 514/34

[56] References Cited

U.S. PATENT DOCUMENTS

| | | | |
|---|---|---|---|
| 4,112,217 | 9/1978 | Henry | 536/6.4 |
| 4,275,192 | 6/1981 | Apple | 536/6.4 |
| 4,291,157 | 9/1981 | Henry | 536/6.4 |
| 4,460,560 | 7/1984 | Rembaum | 424/1.1 |
| 4,671,958 | 6/1987 | McKearn | 424/85 |
| 4,950,738 | 8/1990 | King et al. | 530/322 |

OTHER PUBLICATIONS

Arcamone et al., Int. Symp. on Adriamycin, pp. 9–22 (1972).
Arnon et al., Immunological Rev. 62:5–27 (1982).
Brown, Progress in Med. Chem. 15:125–164 (1978).
Brownlee et al., J. Chem. Soc. Chem. Comm. 1986:659–661 (1986).
Bunton, in Oxidation in Organic Chemistry, vol. I, Wiberg, ed., Academic Press, New York, pp. 367–407 (1965).
Chakravarty et al., J. Med. Chem. 26:638–644 (1983).
Copper et al., J. Biol. Chem. 234:445–448 (1959).
Danon et al., Chem. Abstracts 104:323y (1986).
Dillman et al., Cancer Research 46:4886–4891 (1986).
Dzieduszycka et al., Il Farmaco Ed. Sc. fasc. 11 41:881–891 (1986).
Hurwitz et al., Cancer Research 35:1175–1181 (1975).
Hurwitz et al., Europ. J. Cancer 14:1213–1220 (1978).
Hurwitz et al., Int. J. Cancer 21:747–755 (1978).
Hurwitz Biopolymers 22:557–567 (1983).
Hurwitz et al., J. Med. Chem. 28:137–140 (1985).
Hurwitz et al., J. App. Biochem. 2:25–35 (1980).
Hurwitz et al., Chem. Abstracts 100:167792e (1984).
Ann. N.Y. Aca. Sci. 417:125–136 (1983).
Jackson, in Organic Reactions 2, pp. 341–375 (1944).
March in Advanced Organic Chemistry: Reaction Mechansms and Structure, McGraw Hill Co., New York, pp. 824–827 (1978).
Monsigny et al., FEBS Lett. 119:181–186 (1980).
Scourides et al., J. of Chromatography 288:127–136 (1984).
Tong et al., J. Med. Chem. 21:732–737 (1978).
Trouet et al., Proc. Nat'l Acad. Sci. 79:626–629 (1982).
Weiss et al., Cancer Chemother. Pharmacol. 18:185–197 (1986).

Primary Examiner—Johnnie R. Brown
Assistant Examiner—Elli Peselev
Attorney, Agent, or Firm—Pennie & Edmonds

[57] ABSTRACT

Novel antineoplastic amine-containing derivatives and methods for synthesizing such derivatives of anthracycline antibiotics are disclosed. The derivatives are useful to anthracycline antibiotic conjugates which retain substantial immunospecificity of the unconjugated antibody molecule. Using the conjugates, targeted delivery of the attached antibiotics is achieved in vivo. Such conjugates are thus therapeutically effective against a variety of neoplastic cellular disorders when administered in vivo. Methods for preparing the antibody conjugates and for use of the conjugates in vivo are also disclosed.

2 Claims, 17 Drawing Sheets

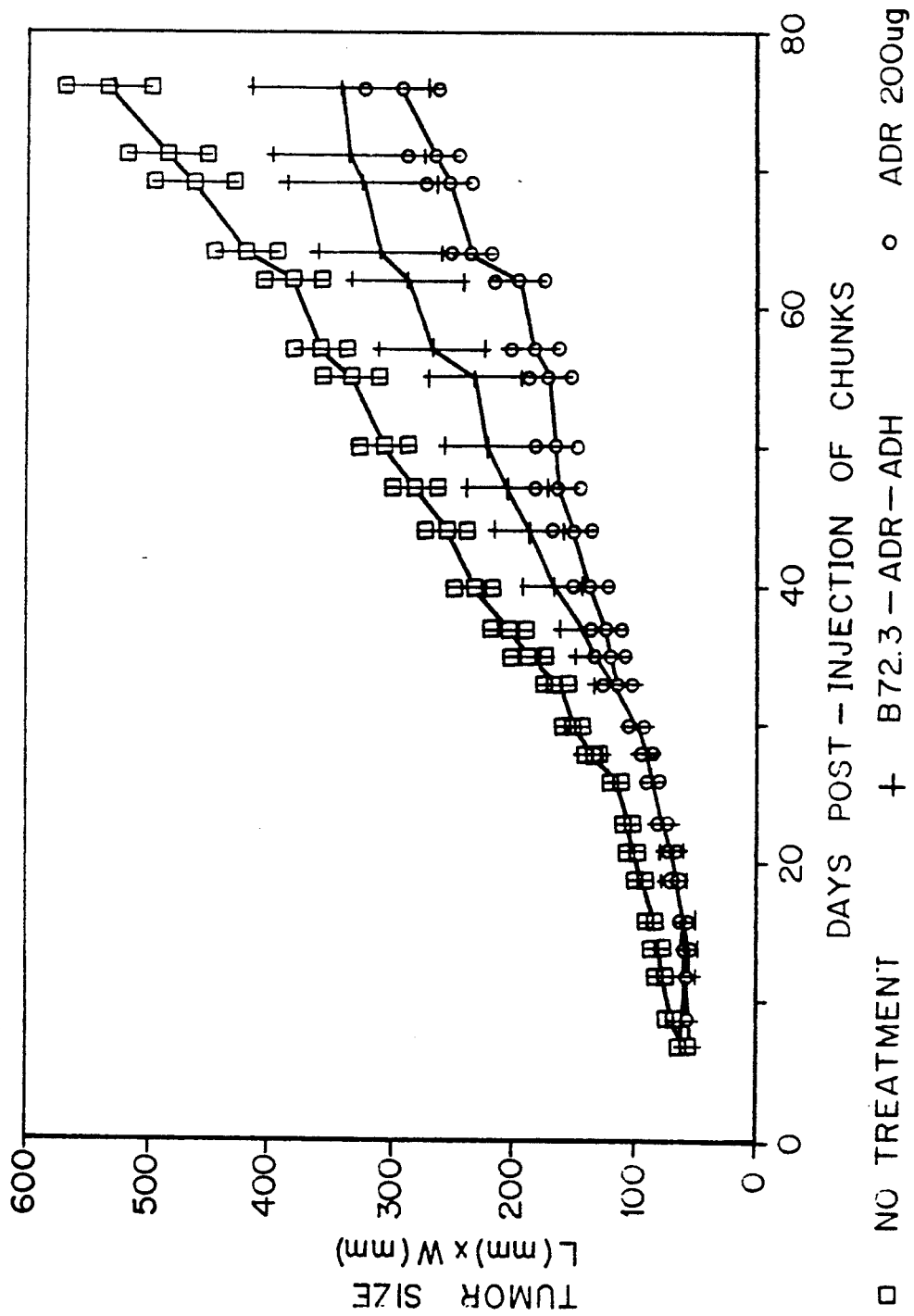

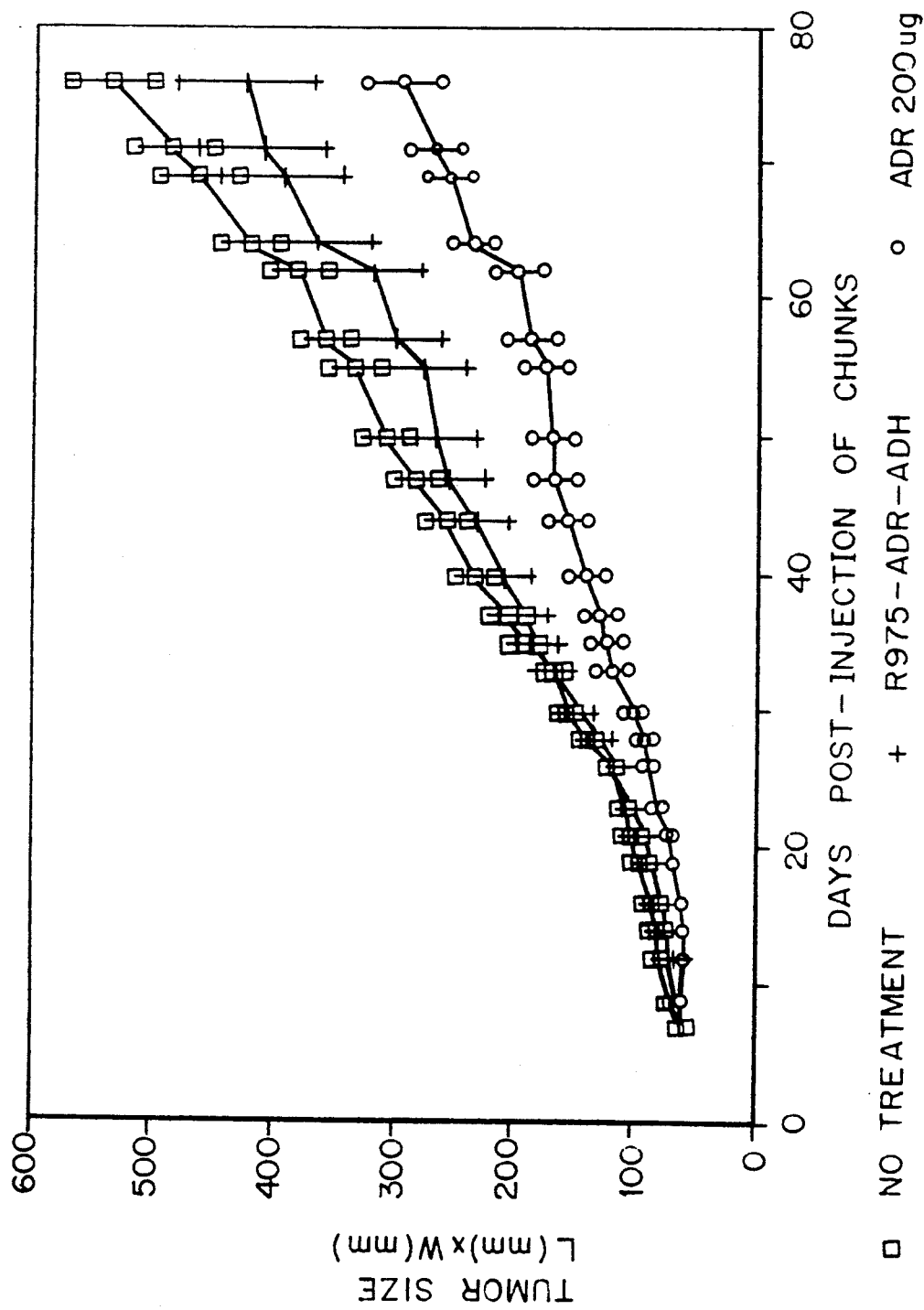

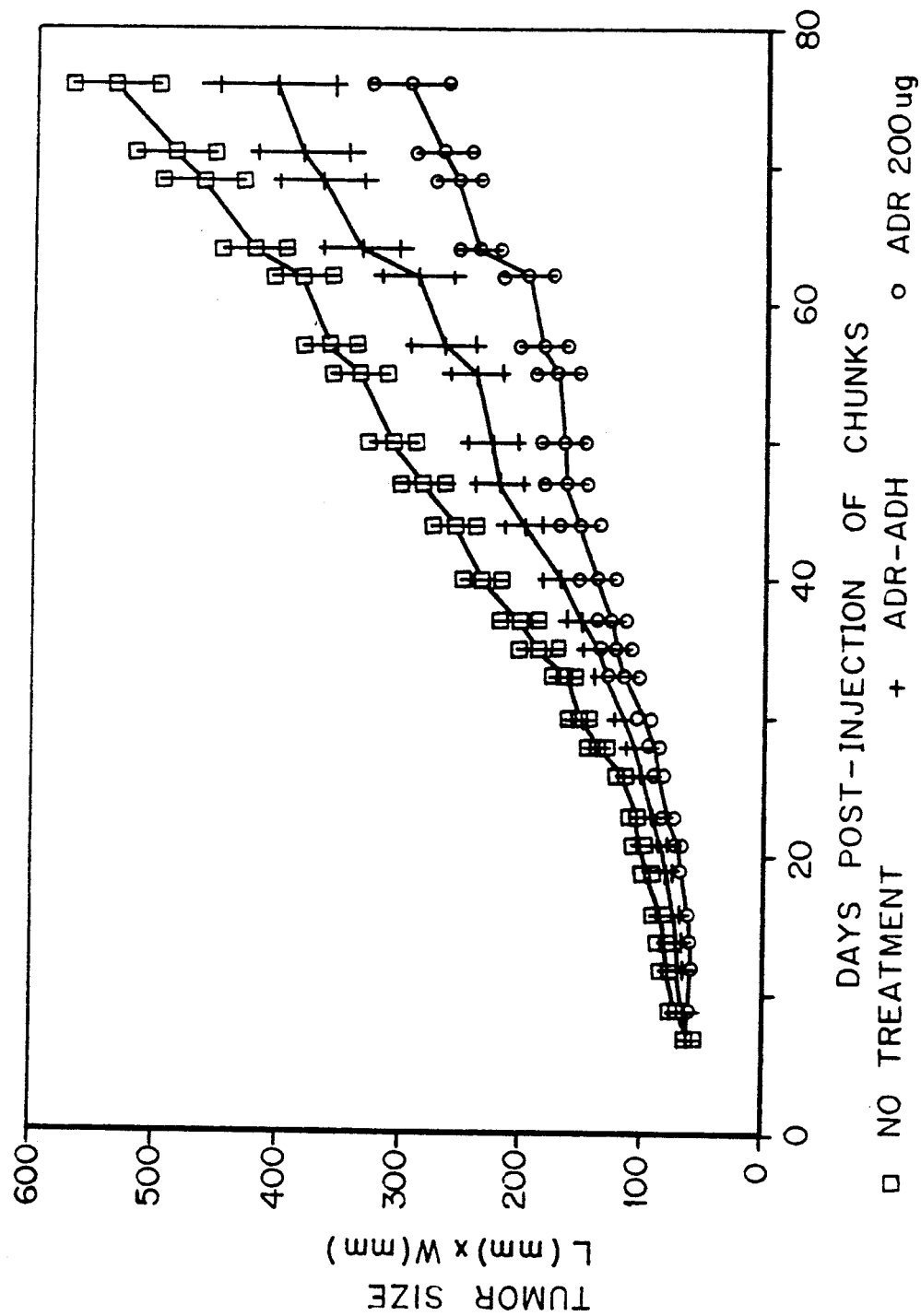

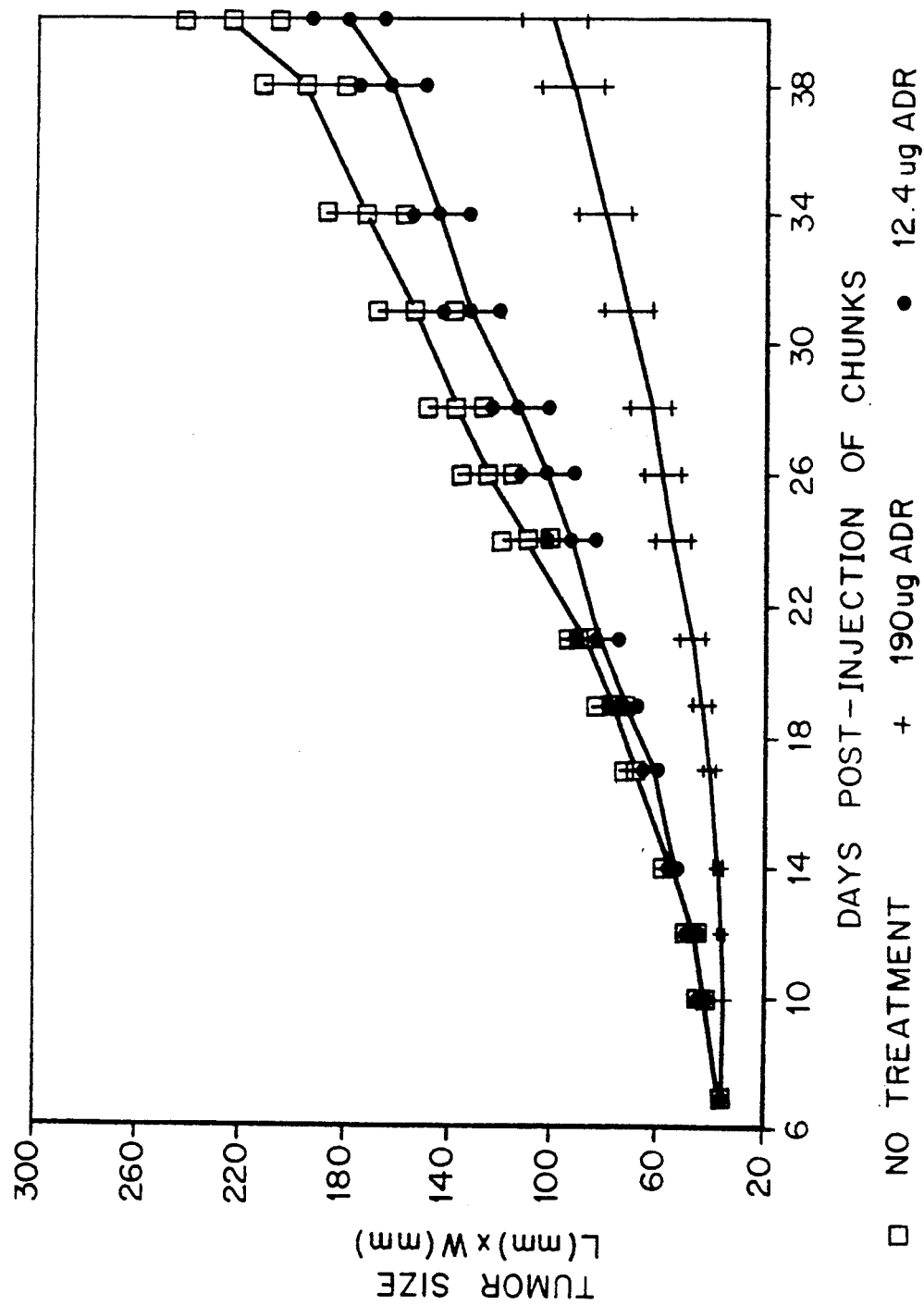

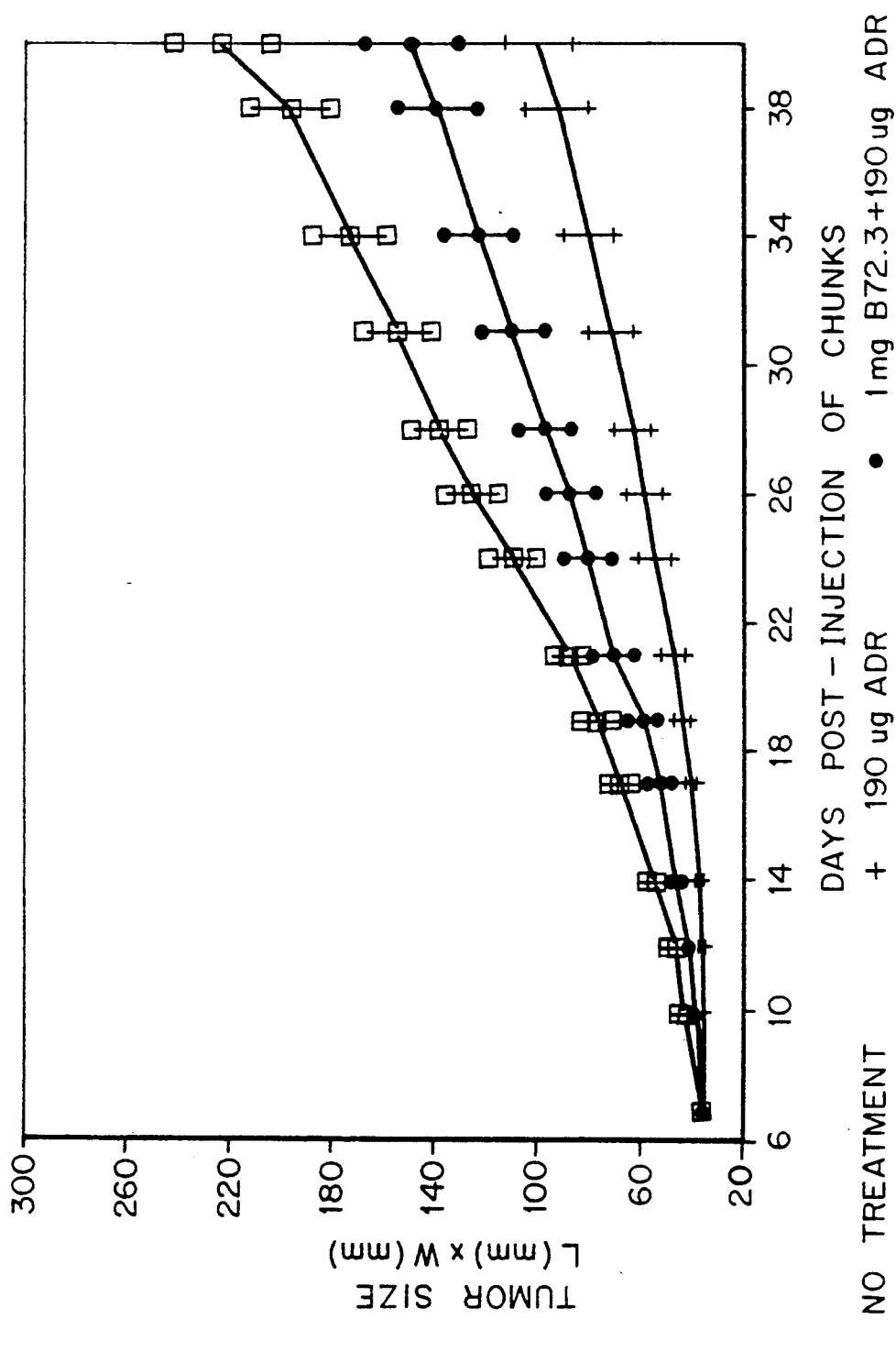

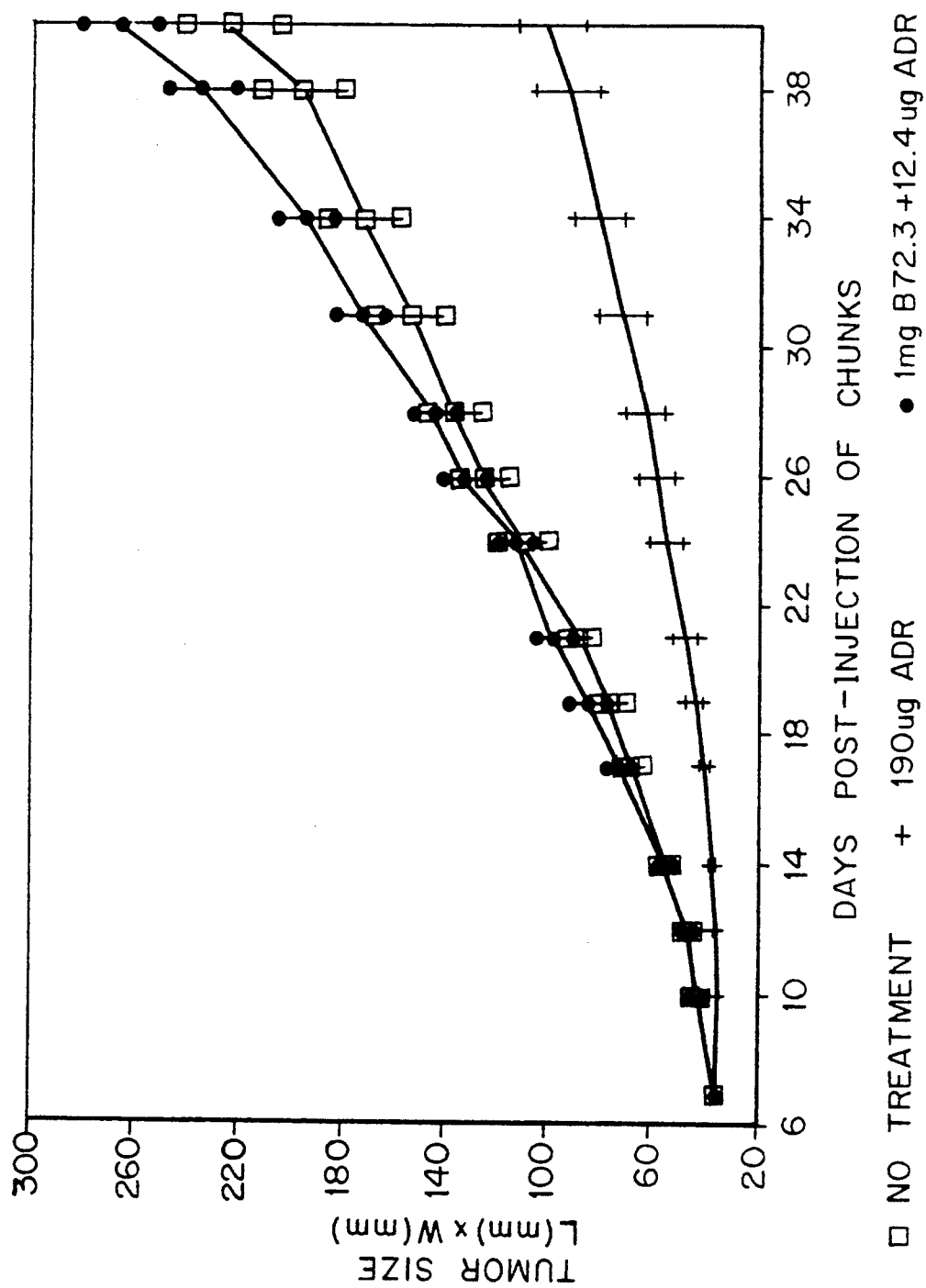

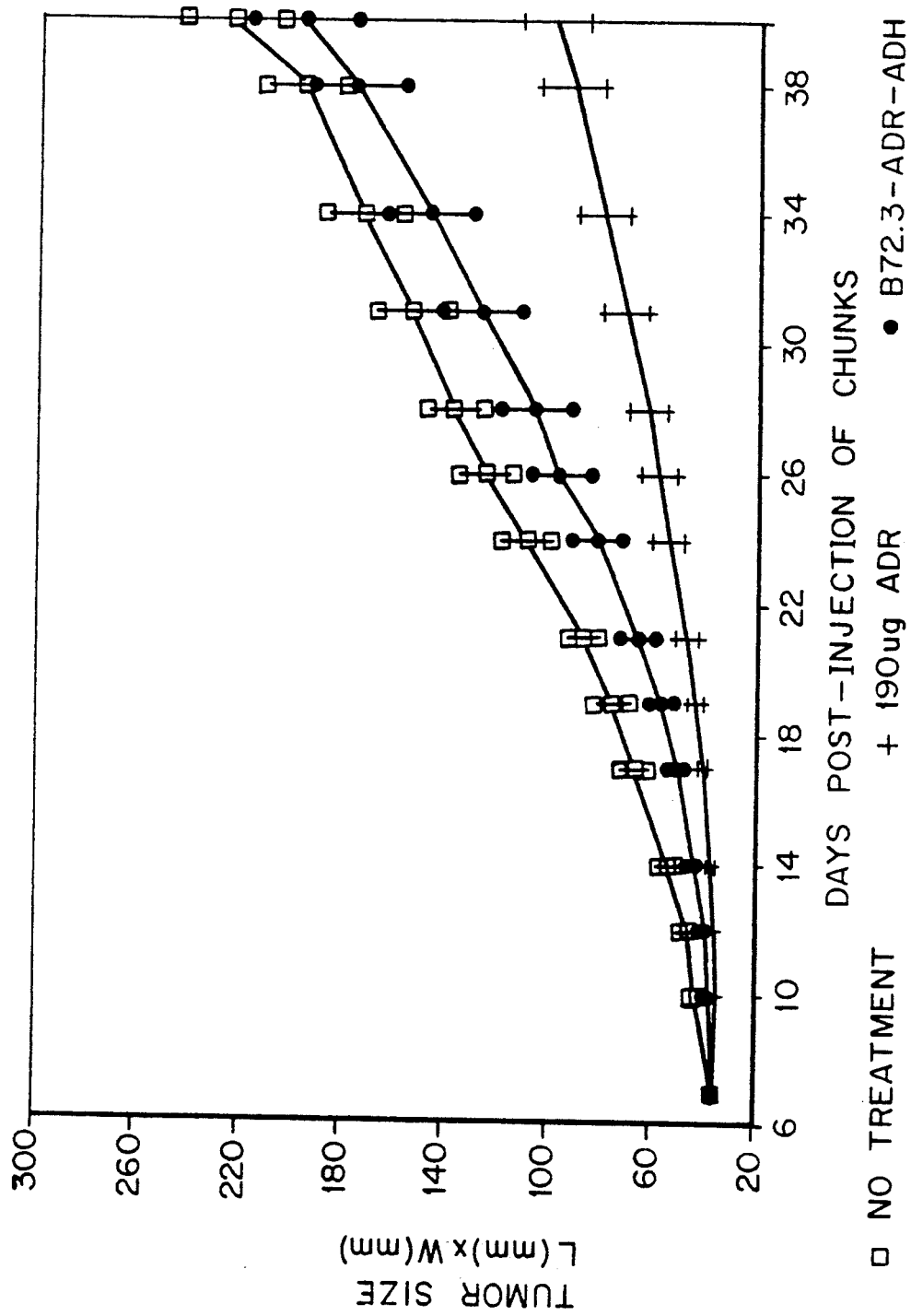

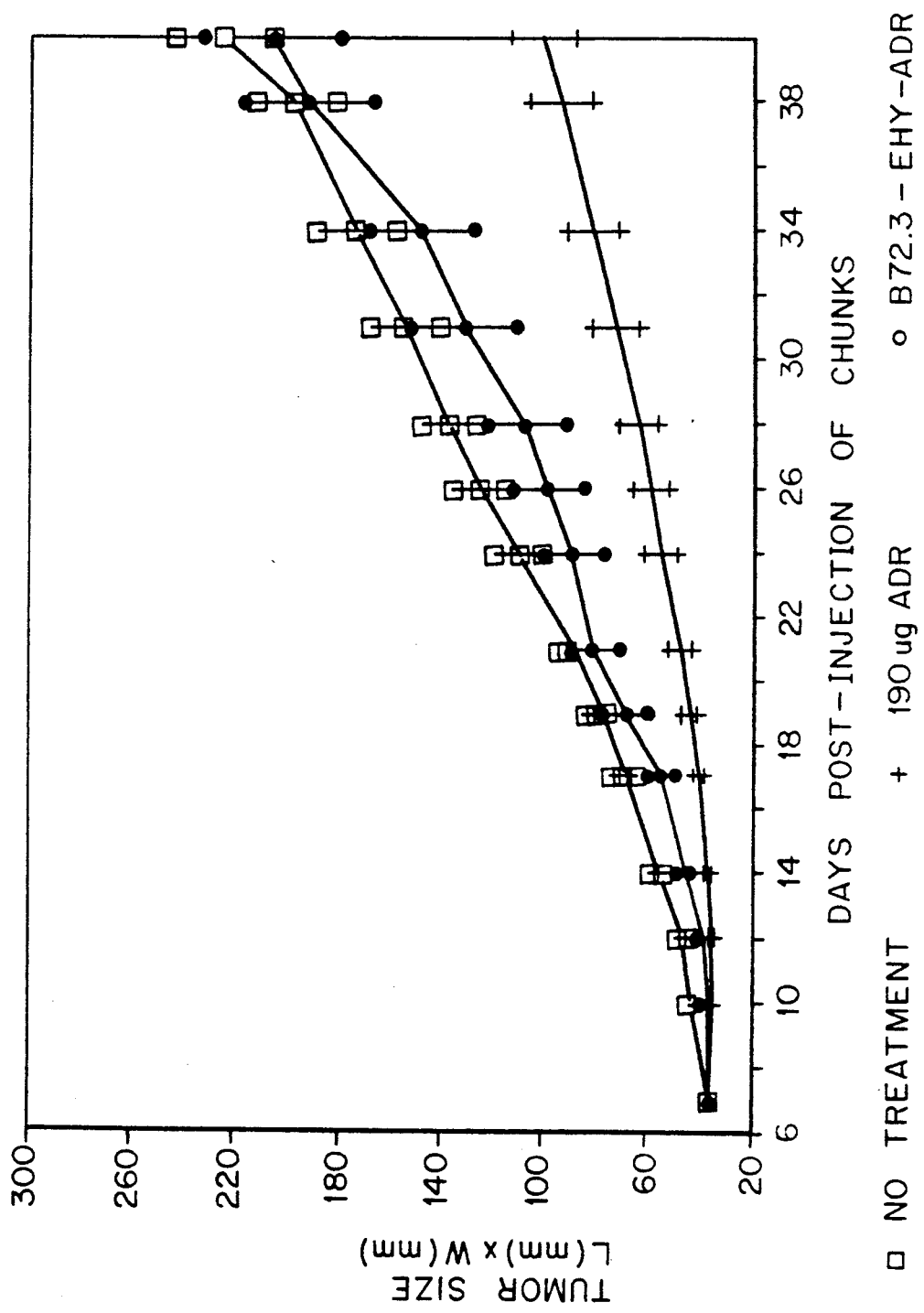

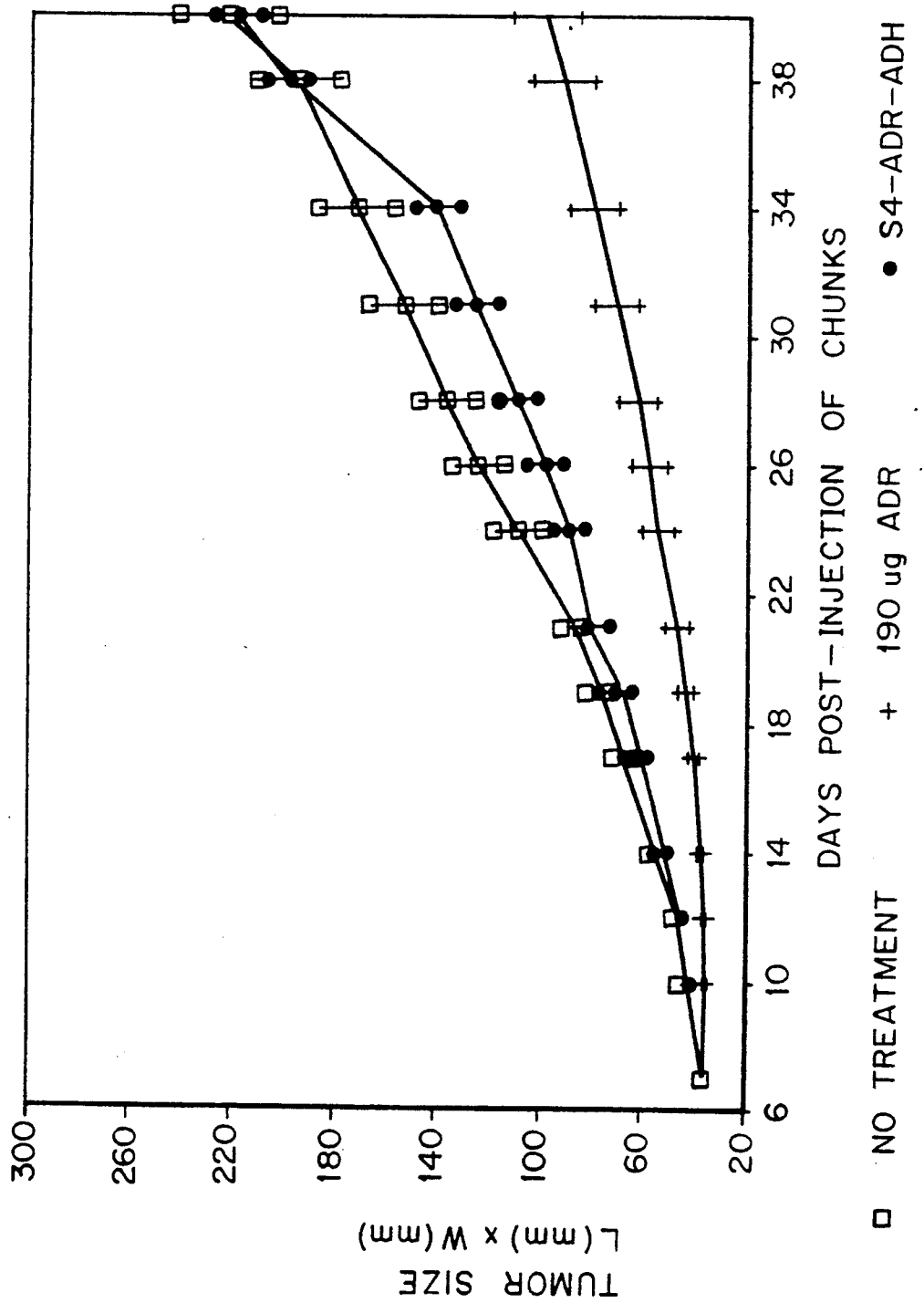

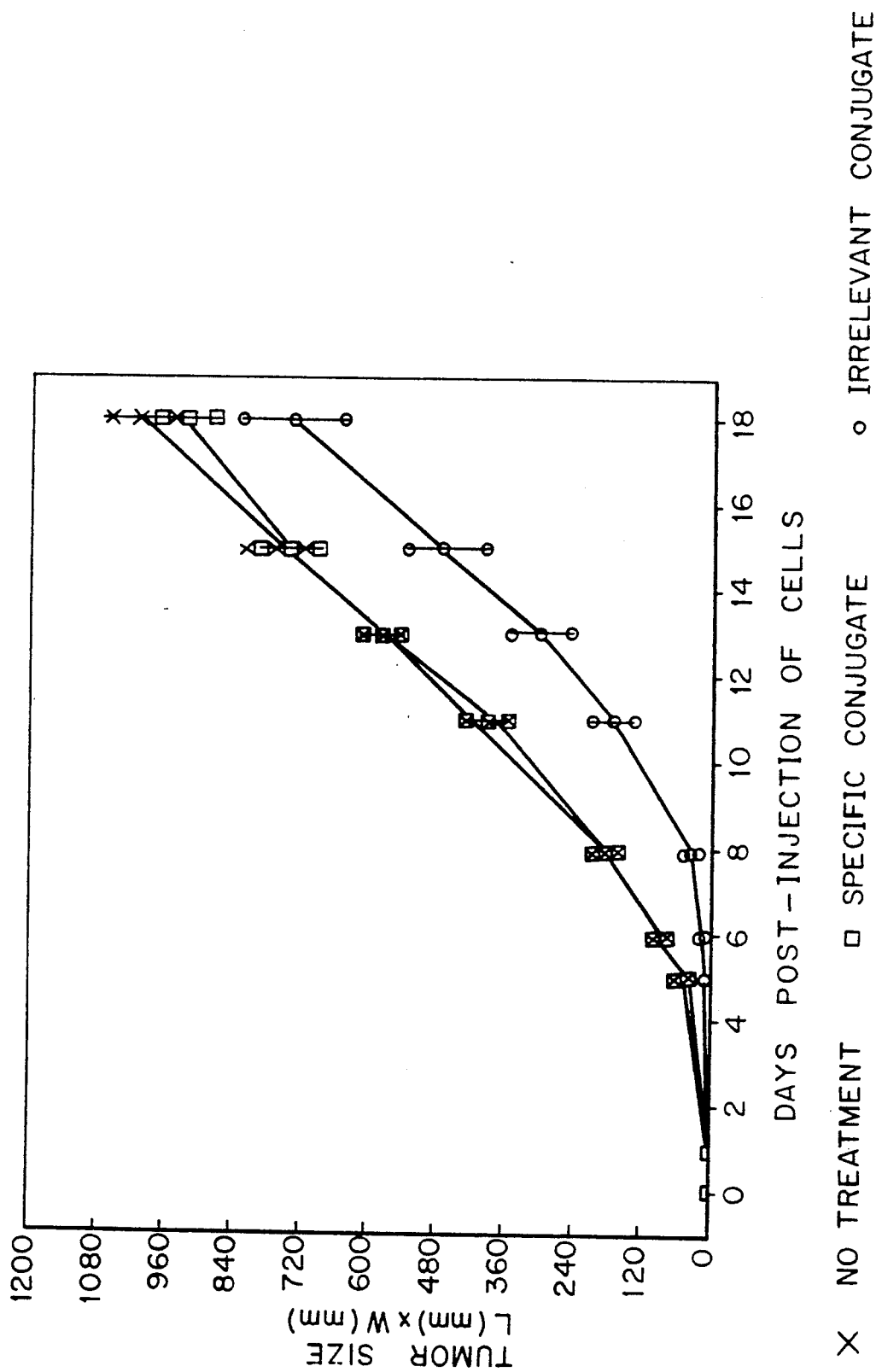

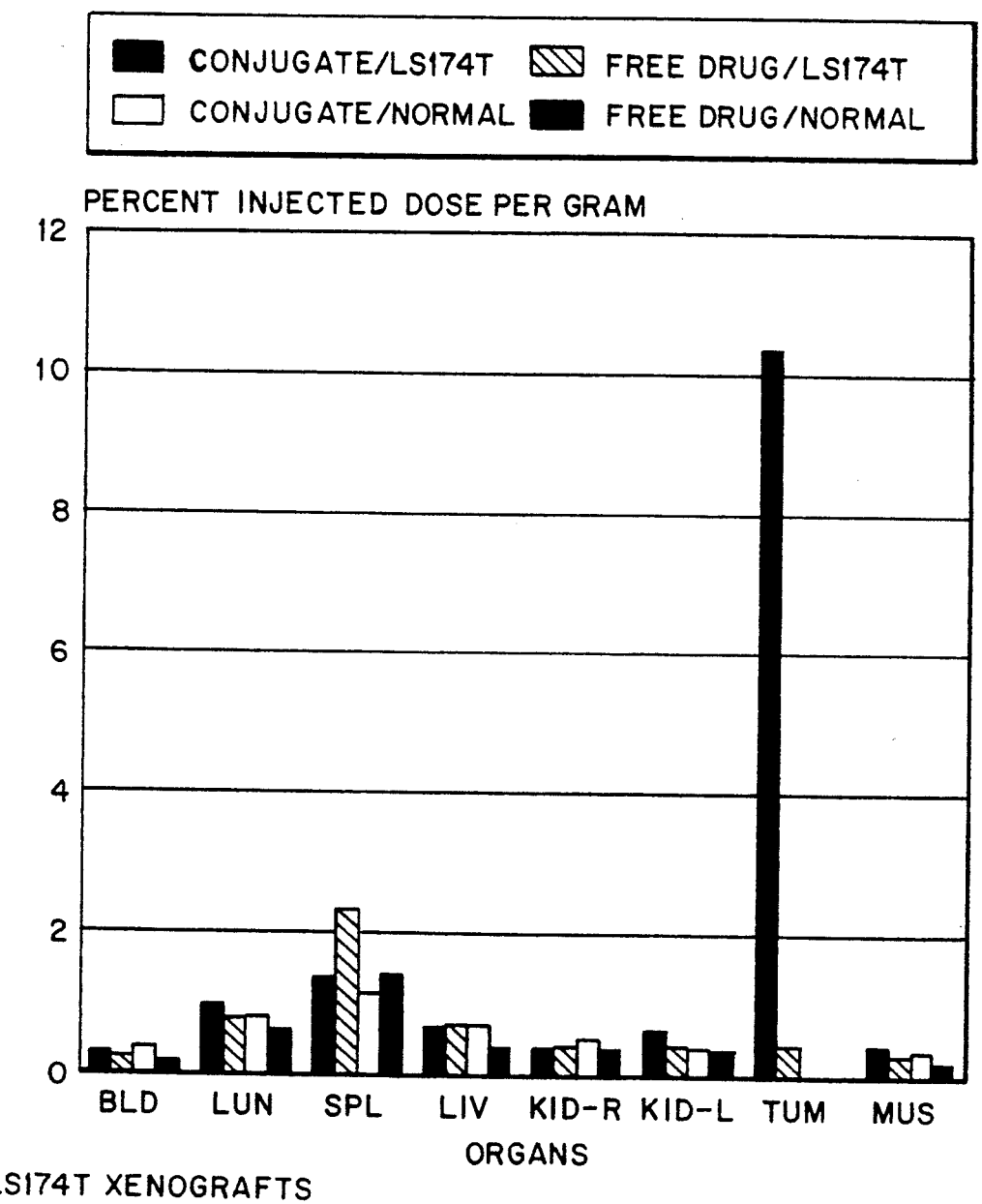

AMINE DERIVATIVES OF ANTHRACYCLINE ANTIBODIES

CROSS REFERENCE TO RELATED APPLICATIONS

This application is a continuation-in-part application of application Ser. No. 058,440 filed on Jun. 5, 1987, currently U.S. Pat. No. 4,950,738, which is a continuation-in-part of Ser. Nos. 650,375, currently U.S. Pat. No. 4,867,973, and 650,754 filed on Sep. 13, 1984, currently abandoned, which in turn is a continuation-in-part of Ser. No. 356,315 filed on Mar. 9, 1982 currently U.S. Pat. No. 4,671,958.

TABLE OF CONTENTS

1. Field of the Invention
2. Background
    2.1 Conjugates of Anthracycline Antibiotics
3. Summary
4. Brief Description of the Figures
5. Definitions
6. Detailed Description of the Invention
    6.1. Amine Derivatives
    6.2. Methods for Synthesis of Amine Derivatives of Anthracycline Antibiotics
    6.3. Methods For Preparing Antibody Conjugates
        6.3.1. Chemical Methods of Oxidation
        6.3.2. Enzymatic Method of Oxidation
        6.3.3. Coupling Oxidized Antibody and an Antineoplastic Amine Derivative of an Anthracycline Antibiotic
        6.3.4. Removal of Aggregates and Non-Covalently Bound Anthracycline Antibiotic
    6.4 Uses of Amine Derivatives of Anthracycline Antibiotics and Antibody Conjugates
7 Synthesis of Amine-Containing Derivatives of Doxorubicin or Adriamycin (ADR)
    7.1. 3' Acyl-ADR Derivatives
        7.1.1. Glycyl-ADR (1)
        7.1.2. Alanyl-ADR (2)
        7.1.3. D-Alanyl-ADR (3)
        7.1.4. Isoleucinyl-ADR (4)
        7.1.5. Valyl-ADR (5)
        7.1.6. Tyrosinyl-ADR (6)
        7.1.7. Arginyl-ADR (7)
        7.1.8. Alanyl-alanyl-ADR (8)
        7.1.9. Alanyl-alanyl-alanyl-ADR (9)
        7.1.10. D-Alanyl-alanyl-alanyl-ADR (10)
        7.1.11. Tyr-Gly-Gly-ADR (11)
        7.1.12. Tyr-Gly-Gly-Arg-ADR (12)
        7.1.13. Tyr-Ala-Ala-Ala-ADR (13)
        7.1.14. Tyr-Val-Leu-Lys-ADR (14)
        7.1.15. Val-Leu-Lys-Val-ADR (15)
        7.1.16. Val-Leu-Lys-Ala-ADR (16)
        7.1.17. Glutamyl-(Gamma-Hydrazide)Alpha-ADR (17)
        7.1.18. Glu-(Alpha-Hydrazide)Gamma-ADR (18)
        7.1.19. Hydrazide Succinyl-Adriamycin (19)
        7.1.20. Hydrazinoacetyl-ADR (20)
        7.1.21. Aminoxyacetyl-ADR (21)
        7.1.22. Hydrazinobenzoyl-ADR (22)
        7.1.23. Hydrazinoacetyl-Tyr-Ala-Ala-Ala-ADR (23)
    7.2. ADR and DNR 13-Hydrazone Derivatives
        7.2.1. Adriamycin-Adipic Dihydrazide (24)
        7.2.2. ADR-Pentaglutamylhydrazide (25)
        7.2.3. Daunorubicin-ADH (26)
        7.2.4. Idarubicin-ADH (27)
        7.2.5. [$^3$H]-Dimethyladriamycin-ADH (28)
    7.3. 14-Thioether DNR Derivative
        7.3.1. DNR-14-S-(3-Propionyl Hydrazide (29)
8. Preparation of Antibody Conjugate
    8.1. ADR-ADH-Antibody Conjugates
    8.2. [$^3$H]Dimethyladriamycin-ADH-Antibody Conjugate
    8.3. Idarubicin-ADH-Antibody Conjugate
    8.4. ADR-Pentaglutamyl Hydrazide Antibody Conjugate
    8.5. ADR-Glu-(Gamma-Hydrazide)-Antibody Conjugate
    8.6. ADR-Glu-(Alpha-Hydrazide)-Antibody Conjugate
9. Therapeutic Effects of Site Selective Adriamycin-Adipic Dihydrazide-Antibody Conjugate
    9.1. Therapeutic Effects Against Human Adenocarcinoma of the Colon
    9.2. Therapeutic Effects Against Lymphoma Xenografts
10. Biodistribution of B72.3-[$^3$H]-Me$_2$ADR-ADH

1. FIELD OF THE INVENTION

The present invention relates to novel amine derivatives of anthracycline antibiotics. More particularly, the invention encompasses amine-containing derivatives of anthracycline antibiotics having antineoplastic activity which can be covalently attached to an antibody or antibody fragment via a reactive amine group of the anthracycline derivative. Methods for preparing novel derivatives of anthracycline antibiotics and antibody conjugates as well as methods for using the antibody conjugates are described.

2. BACKGROUND

Anthracycline antibiotics, especially daunorubicin and doxorubicin have important therapeutic efficacy against acute leukemias and a variety of neoplasms including a number of solid tumors. As with most antineoplastic chemotherapeutic agents, the anthracycline antibiotics exhibit a number of toxic manifestations including bone marrow depression, stomatitis, alopecia, gastrointestinal disturbances and sometimes dermatological mainifestations. In addition, cardiac toxicity is a unique adverse characteristic of anthracycline antibiotics. Two forms of cardiac toxicity have been observed: (1) an acute form characterized by abnormal ECG changes including ST-T alterations and arrhythmias; and (2) chronic, cumulative dose-related toxicity characterized by congestive heart failure unresponsive to digitalis. In sum, cardiac toxicity is manifested by tachycardia, arrhythmias, dyspnea, hypotension and congestive heart failure which does not respond to digitalis. The cumulative, dose-limiting cardiotoxicity is a major obstacle to the therapeutic use of the anthracycline antibiotics.

Thus, there has been a long-felt need for analogs and/or derivatives of anthracycline antibiotics which maintain therapeutic efficacy against neoplasms but have diminished or eliminated cardiotoxicity. For a general review of derivatives of anthracycline antibiotics that have been developed with a view to lowering cardiotoxicity, see Weiss et al., 1986, Cancer Chemother. Pharmacol 18:185-97 and references cited therein.

In an attempt to prepare anthracycline antibiotic derivatives to serve as prodrugs which would be selective substrates for the enzyme plasmin which is often found in elevated levels at solid tumor sites, Chakravarty et al., (1983, J. Med. Chem. 26:638-44) synthesized 3' peptidyl derivatives of doxorubicin. For example, 3'-(D-val-L-leu-L-lys)-doxorubicin was obtained using a mixed anhydride of the protected FMOC-peptide in isobutyl chloroformate followed by removal of the FMOC group using anhydrous ammonia.

Other investigators have prepared C-13 bis-hydrazone derivatives of anthracycline antibiotics. For example, U.S. Pat. No. 4,112,217 issued to Henry et al. describes C-13 bis-hydrazone derivatives of doxorubicin and daunorubicin formed by reacting an excess molar amount of either doxorubicin or daunorubicin with an acid hydrazide. More recently, Brownler et al. (1986, J. Chem. Soc. Chem. Comm. 1986:659-61) describes synthesis of a mono-hydrazone adduct of daunorubicin having a free hydrazide moiety which was formed by reaction of daunorubicin hydrochloride and a dihydrazide of the formula

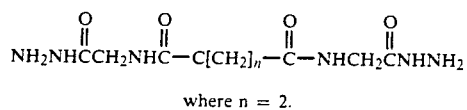

where n = 2.

2.1. CONJUGATES OF ANTHRACYCLINE ANTIBIOTICS

Alternatively, in attempts to reduce cardiotoxicity, anthracycline antibiotics such as daunorubicin or doxorubicin have been covalently linked to antibodies, Fab dimers, or to lectins by non-site specific or random coupling methods such as glutaraldehyde, carbodiimide and periodate oxidation of the drug (see Monsigny et al., 1980, FEBS Lett. 119:181-186 and references cited therein).

Hurwitz et al., (1980, J. App. Biochem. 2:25-35) describes antibody-daunorubicin conjugates prepared by a two-stage process. First, carbohydrate moieties of the Fc region of goat serum immunoglobulin were oxidized using periodic acid and the resulting aldehyde groups reacted with polyglutamylhydrazide to form aqueous-soluble antibody-polyglutamylhydrazide macromolecules. In some instances, the macromolecules were reduced using sodium cyanoborohydride to convert hydrazone bonds to stable hydrazido groups. Second, the antibody polyglutamylhydrazide macromolecules were then reacted with daunorubucin to form antibody-daunorubicin conjugates. In complete contrast to the present antibody-anthracycline conjugates characterized by aqueous solubility such that they are suitable and advantageously used for administration in vivo, Hurwitz et al's conjugates in all cases became insoluble and were completely unsuitable for administration in vivo.

3. SUMMARY

The present invention encompasses novel antineoplastic amine-containing derivatives of anthracycline antibiotics such as derivatives of daunorubicin, doxorubicin, epirubicin, esorubicin, idarubicin, carminocyin, 4-demethoxy-4'-O-methyldoxorubicin, 4'-O-tetrahydropyranyldoxorubicin, 3'-deamino-3'(3"-cyano-4"-morpholinyl) doxorubicin, etc., in which the amine moiety comprises a reactive amine selected from the group consisting of hydrazine, hydrazide, phenylhydrazine, phenylhydrazide, alkoxyamine, phenoxyamine, semicarbazide and thiosemicarbazide. The derivatives are particularly useful for preparation of aqueous soluble therapeutic antibody conjugates for the treatment of cellular disorders.

The therapeutic amine-containing anthracycline antibiotic derivatives are covalently attached to an antibody or antibody fragment. The covalent attachment is accomplished so that the resulting antibody conjugate possesses both the ability to bind antigen and exert therapeutic effectiveness when administered in vivo. In particular, covalent attachment is accomplished by forming a covalent bond between an oxidized carbohydrate moiety of an antibody or antibody fragment and a reactive amine on a derivative of an anthracycline antibiotic in which the amine is selected from the group consisting of hydrazine, hydrazide, phenylhydrazine, phenylhydrazide, alkoxyamine, phenoxyamine, semicarbazide and thiosemicarbazide. Thus the invention encompasses antibody-anthracycline conjugates, comprising an amine-containing anthracycline antibiotic derivative attached via a covalent bond to an oxidized carbohydrate moiety of an antibody or antibody fragment, in which the conjugate is characterized by (1) aqueous solubility such that the conjugate is suitable for in vivo administration; and (2) substantially the same immunospecificity as the unconjugated antibody or antibody fragment and in which the covalent bond is selected from the group consisting of hydrazone, phenylhydrazone, acyl hydrazone, oxime, semicarbazone, thiosemicarbazone and derivatives thereof.

The invention further encompasses a method for preparing site selective therapeutic antibody conjugates, comprising:

(a) reacting an antibody or antibody fragment with an oxidizing agent to form an aldehyde group in the carbohydrate moiety of the antibody or antibody fragment; and (b) reacting the aldehyde group of the oxidized carbohydrate of the antibody or antibody fragment with a reactive amine group of an amine-containing anthracycline antibiotic in which the reactive amine is selected from the group consisting of hydrazine, hydrazide, phenylhydrazine, phenylhydrazide, alkoxyamine, phenoxyamine, semicarbazide and thiosemicarbazide to form a conjugate characterized by: (1) aqueous solubility such that the conjugate is suitable for in vivo administration; and (2) substantially the same immunospecificity as the unconjugated antibody or antibody fragment.

In addition the invention encompasses a method for preparing site selective therapeutic antibody conjugates, comprising: reacting an aldehyde group of an oxidized carbohydrate of an antibody or antibody fragment with a reactive amine group of an amine-containing anthracycline antibiotic in which the reactive amine is selected from the group consisting of hydrazine, hydrazide, phenylhydrazine, phenylhydrazide, alkoxyamine, phenoxyamine, semicarbazide and thiosemicarbazide to form a conjugate characterized by: (1) aqueous solubility such that the conjugate is suitable for in vivo administration; and (2) substantially the same immunospecificity as the unconjugated antibody or antibody fragment.

The aqueous soluble antibody conjugates of the present invention are particularly suited for in vivo therapy of cellular disorders by delivering an anthracycline antibiotic to a desired target site. Thus the invention further encompasses methods for treating cellular disorders which comprise, administering, to an animal or a human, a therapeutically effective amount of an aqueous soluble anthracycline antibiotic-antibody conjugate, in which the conjugate is immunospecific for an antigenic determinant of a target associated with a cellular disorder and substantially non-immunospecific for non-target sites and in which the antigenic determinant is not found in substantial amount in non-target sites. The target sites include specific cells, tissues, organs or any other sites in vivo associated with cellular disorders amenable to treatment with an anthracycline antibiotic or a derivative thereof. The cellular disorders which can be treated include, but are not limited to: acute lymphocytic leukemia, acute granulocytic leukemia, acute monolymphoblastic leukemia, malignant lymphomas including, but not limited to non-Hodgkin's lymphomas, carcinomas including but not limited to carcinoma of the breast, small (oat)-cell carcinoma, carcinoma of the bladder, bronchiogenic carcinoma, metastatic thyroid carcinoma and carcinomas of the endometrium, testes, prostate, cervix and head and neck; sarcomas including but not limited to osteogenic sarcoma, Ewing's sarcoma, and soft-tissue sarcomas, metastatic adenocarcinoma of the breast, and plasma cell myeloma.

4. BRIEF DESCRIPTION OF THE FIGURES

Figure 1B:
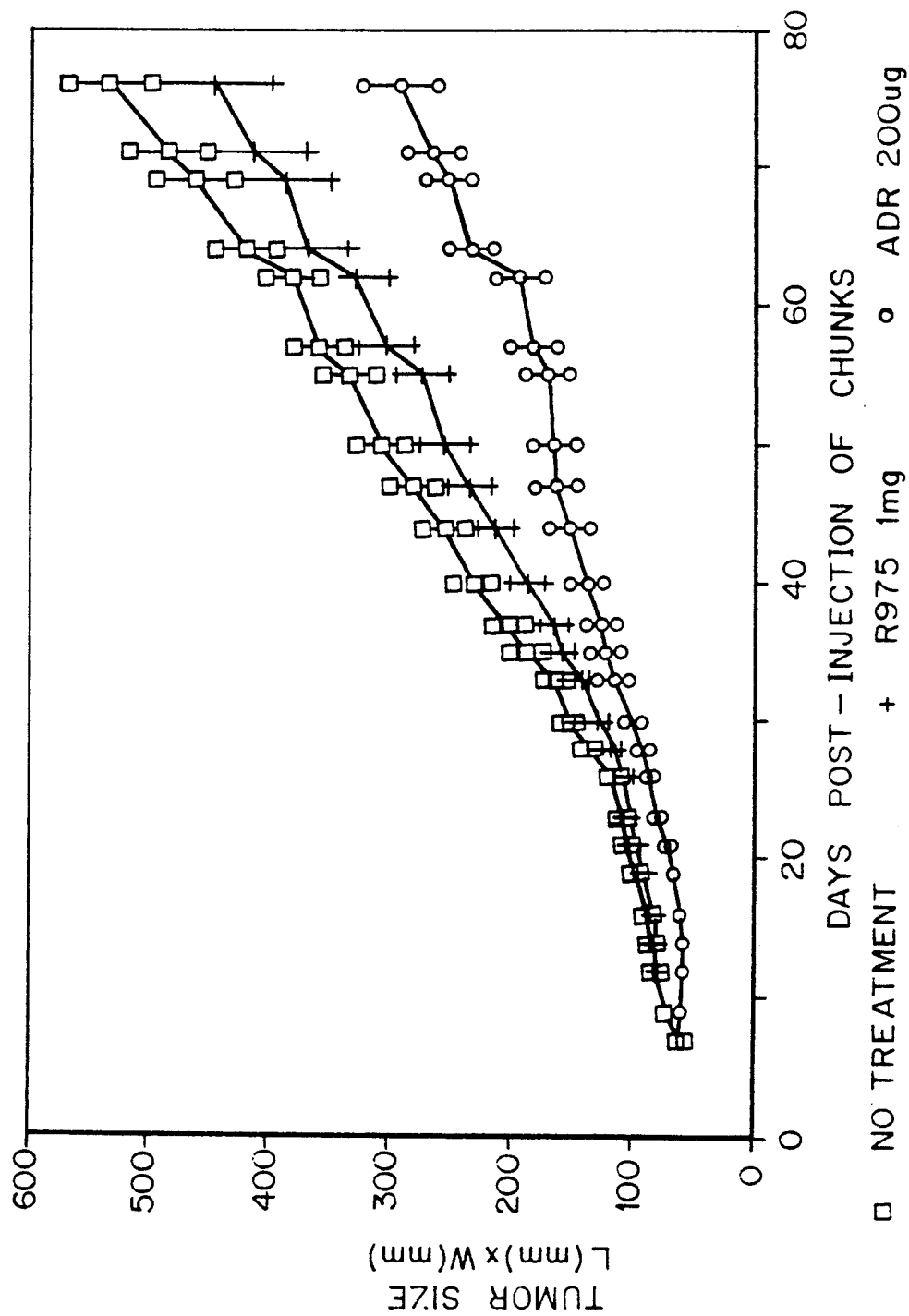
Figure 1F:
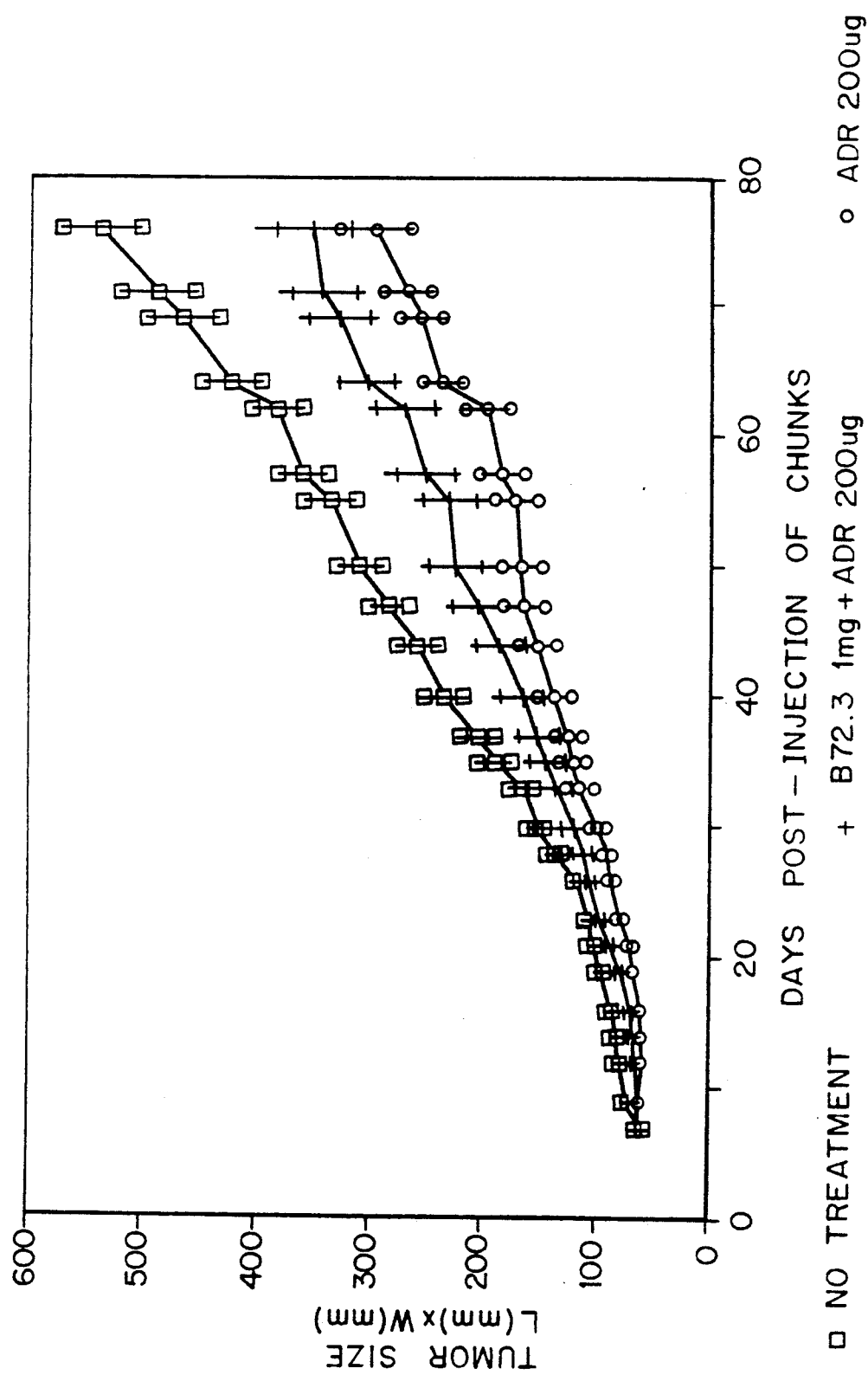

The present invention may be understood more fully by reference to the following detailed description of the invention, examples of specific embodiments of the invention and the appended figures in which:

FIG. 1(A-F) graphically illustrates therapeutic efficacy of a site selective adriamycin-adipic dihydrazide (ADR-ADH) tumor specific antibody conjugate against a human adenocarcinoma xenograft. (A) tumor-specific antibody alone; (B) non-specific or irrelevant antibody alone; (C) tumor specific ADR-ADH-antibody conjugate; (D) non-specific ADR-ADH antibody conjugate; (E) ADR-ADH alone; and (F) a mixture of tumor specific antibody and ADR. Tumor growth in untreated control animals and in animals treated with ADR at about maximum tolerated dose (mtd) is included for comparison (A-F).

Figure 2A:
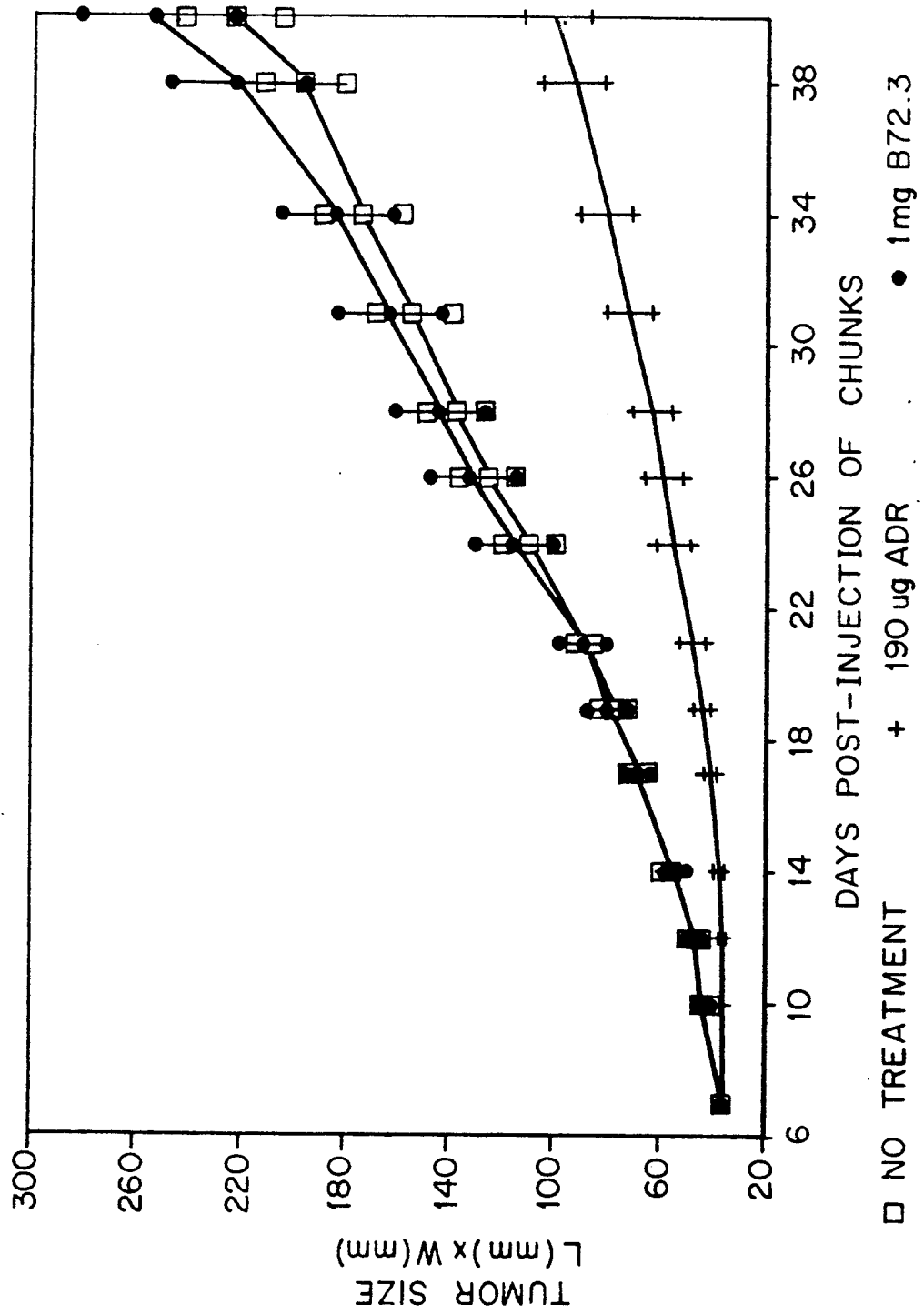

FIG. 2(A-H) graphically illustrates therapeutic efficacy of a site selective ADR-ADH-tumor specific antibody conjugate and of a site selective adriamycin-(glutamylgamma-hydrazide) (ADR-E-gamma-Hy) tumor specific antibody conjugate against the human adenocarcinoma xenograft. (A) tumor-specific antibody alone; (B) ADR alone, low dose; (C) tumor specific antibody plus ADR (mtd) mixture; (D) tumor specific antibody plus ADR (low dose) mixture; (E) tumor specific ADR-ADH-antibody conjugate; (F) tumor specific ADR-E-Hy antibody conjugate; (G) non-specific ADR-ADH antibody conjugate; and (H) non-specific ADR-E-Hy-antibody conjugate. Tumor growth in untreated control animals and in animals treated with ADR at about maximum tolerated dose (mtd) is included for comparison (A-H).

FIG. 3(A-B) is a graphic illustration of the therapeutic efficacy of site selective ADR-ADH tumor specific antibody conjugate against a lymphoma xenograft. (A) tumor specific antibody-ADR-ADH-conjugate; non-specific ADR-ADH antibody conjugate; no treatment; (B) tumor specific antibody alone; ADR-ADH alone; and a mixture of tumor specific antibody and ADR.

FIG. 4 is a graphic illustration of the biodistribution of [$^3$H]-Me$_2$ADR-ADH tumor specific antibody conjugate against the human adenocarcinoma xenograft into the blood, lungs, spleen (spl), livers (liv), right and left kidneys (KID-R and KID-L), muscle and tumors of four group of mice. Groups 1 and 2 were administered with human adenocarcinoma xenografts in vivo whereas groups three and four were untreated. Groups 1 and 3 were administered with [$^3$H]-Me$_2$ADR-ADH tumor specific antibody conjugate. Groups 2 and 4 with administered with [$^3$H]-Me$_2$ADR-ADH alone.

5. DEFINITIONS

As used throughout the present specification, the term "anthracycline antibiotic" is intended to encompass any antineoplastic agent having a tetracyclic quinoid ring structure including but not limited to such agents in which the ring structure is coupled via a glycosidic linkage to a sugar such as daunosamine and derivatives thereof. Thus "anthracycline antibiotics" encompass daunorubicin, doxorubicin, epirubicin, esorubicin, idarubicin, carminomycin, 4-demethoxy-4'-O-methyl doxorubicin, 4'-O-tetrahydropyranyl-doxorubicin, 3'-deamino-3'-(3"-cyano-4"-morpholinyl) doxorubicin, aclacinomycin and any antineoplastic analogs thereof.

The term "amine derivative of an anthracycline antibiotic" is intended to encompass any antineoplastic anthracycline antibiotic that contains or is modified to contain a reactive amine.

The term "reactive amine" is intended to encompass any nitrogen-containing functional group that can be covalently attached or bonded through a nitrogen atom to an aldehyde functional group by a simple chemical condensation reaction. Examples of such reactive amines include but are not limited to: hydrazine, hydrazide, phenylhydrazine, phenylhydrazide, alkoxyamine, phenoxyamine, semicarbazide and thiosemicarbazide.

6. DETAILED DESCRIPTION OF THE INVENTION

The present invention concerns antineoplastic derivatives of anthracycline antibiotics having a reactive amine which can be site selectively covalently attached to an oxidized carbohydrate moiety of an antibody or antibody fragment to form aqueous soluble therapeutic antibody conjugates.

In one embodiment of the present invention, a reactive amine group is attached via a linking moiety, including but not limited to an amino acid, a peptide, an organic acid moiety of the formula $-CO(CH_2)_nCO-$ where $n=2-3$, and an organic moiety of the formula $-Z-CONH-X$ in which Z is

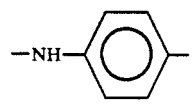

$-OCH_2-$
$-NH-CH_2-$
$-NHCOCH_2CH_2CH(NH_2)-$
or
$-NHCOCH(NH_2)CH_2CH_2-$ and X is an amino acid or a peptide, to a primary or secondary amine group on the sugar moiety such as the 3'amino group of the sugar moiety of daunorubicin, doxorubicin, idaurubicin, epirubicin, esorubicin, carminomycin, 4-demethoxy-4'-O-methyl doxorubicin, 4'-O-tetrahydropyranyl doxorubicin, or 3'-deamino-3'-(3''-cyano-4''-morpholinyl) doxorubicin.

In another embodiment, the reactive amine group is attached via a linking moiety, including but not limited to an amino acid, peptide or a reactive amine which is a hydrazide moiety of the formula $H_2N\text{—}NHCO\text{—}[R\text{—}]\text{—}CO\text{—}$ in which R is an alkylene chain with 0–20 carbon atoms in the chain, to the C-13 keto group of daunorubicin, doxorubicin, epirubicin, esorubicin, idarubicin, carminomycin, 4-demethoxy-4'-O-methyl doxorubicin, 4'-O-tetrahydropyranyl doxorubicin, 3'-deamino-3'-(3''-cyano-4''-morpholinyl) doxorubicin, and analogs thereof via a simple chemical condensation reaction.

In yet another embodiment, the reactive amine group is attached either via a thioether or tertiary amine linkage to the C-14 methylene group of daunorubicin, idarubicin or carminomycin and other antineoplastic anthracycline antibiotic analogs having a suitable methylene group.

6.1. AMINE DERIVATIVES

Amine derivatives of anthracycline antibiotics useful according to the present invention encompass derivatives of naturally occurring and synthetic antineoplastic anthracycline antibiotics which either contain or are modified to contain a reactive amine moiety. Table I presents a non-exhaustive list of examples of antineoplastic anthracycline antibiotics.

TABLE I
| ANTHRACYCLINE ANTIBIOTICS |
| --- |
| Daunorubicin (DNR) |
| Doxorubicin (Adriamycin, ADR) |
| Epirubicin |
| Esorubicin |
| Idarubicin |
| Carminomycin |
| 4-Demethoxy-4'-O-methyl doxorubicin |
| 4'-o)-Tetrahydropyranyl doxorubicin |
| 3'-Deamino-3'-(3''-cyano-4''-morpholinyl) doxorubicin |

The term "reactive amine" moiety is intended to encompass any nitrogen-containing functional group that can be covalently attached or bonded through a nitrogen atom to an aldehyde functional group by a simple condensation reaction. Thus, amine derivatives of anthracycline antibiotics useful according to the invention include but are not limited to:
glutamyl-(gamma-hydrazide)-alpha-adriamycin (ADR-E-gamma Hy); glutamyl-(alpha-hydrazide)-gamma-adriamycin; hydrazide-succinyl-adriamycin; hydrazinoacetyl-adriamycin; aminoxyacetyl-adriamycin; hydrazinobenzoyl-adriamycin; hydrazinoacetyl-tyrosinyl-alanyl-alanyl-alanyl-adriamycin; adriamycin-adipic dihydrazide (ADR-ADH); dimethyladriamycin-adipic dihydrazide; idarubicin-adipic dihydrazide; adriamycin-pentaglutamylhydrazide; daunorubicin-adipic dihydrazide; daunorubicin-14-S-(3-propionyl hydrazide); daunorubicin-14-N-methyl-(acetyl hydrazide); etc.

Acyl derivatives of anthracycline antibiotics which can be further derivatized using Scheme 1a (infra) to yield derivatives of anthracycline antibiotics containing a reactive amine which are useful according to the present invention include but are not limited to: glycyl-adriamycin; alanyl-adriamycin; D-alanyl-adriamycin; isoleucinyl-adriamycin; valyl-adriamycin; tyrosinyl-adriamycin; arginyl-adriamycin; alanyl-alanyl-adriamycin; alanylalanyl-alanyl-adriamycin; D-alanyl-alanyl-alanyl-adriamycin; tyrosinyl-glycyl-glycyl-adriamycin; tyrosinyl-glycyl-glycyl-arginyl-adriamycin; tyrosinyl-alanyl-alanyl-alanyl-adriamycin; tyrosinyl-valyl-leucyl-lysyl-adriamycin; valyl-leucyl-lysyl-alanyl-adriamycin; valyl-leucyl-lysyl-valyl-adriamycin; etc. These acyl derivatives are also useful for research purposes.

6.2. METHODS FOR SYNTHESIS OF AMINE DERIVATIVES OF ANTHRACYCLINE ANTIBIOTICS

The amine derivatives of anthracycline antibiotics useful according to the present invention can be synthesized using a variety of methods.

According to one method, acyl derivatives of anthracycline antibiotics containing a reactive amine are synthesized according to the reaction scheme illustrated below (Scheme 1) in which R represents an active ester moiety derived from N-hydroxysuccinimide or N-hydroxybenzotriazole; a mixed carbonic-carboxylic anhydride derived from isobutylchloroformate; or a chlorine atom. For convenience, Scheme 1 is presented using the anthracycline antibiotic adriamycin (ADR). The method however, is not limited to this compound, but rather can be used to prepare acyl derivatives of any anthracycline antibiotic having a primary or secondary amine group on the sugar moiety including daunorubicin (DNR), idarubicin, epirubicin, esorubicin, carminomycin, 4-demethoxy-4'O-methyl doxorubicin, 4'-O-tetrahydropyranyl doxorubicin, etc. as well as ADR which has an amine in the 3' position on the daunosamine sugar moiety.

SCHEME 1

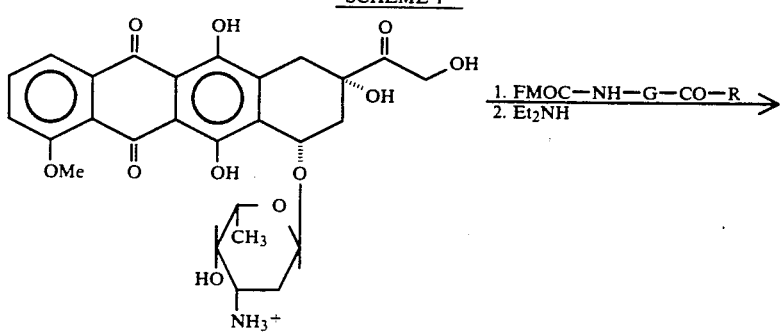

SCHEME 1
-continued

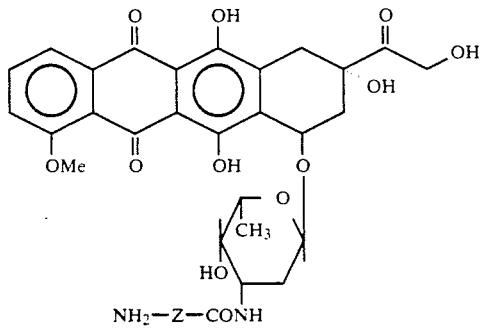

in which

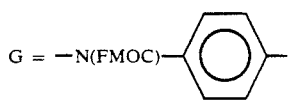 and 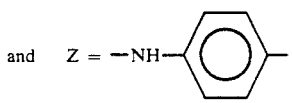

G = —N(FMOC)—CH$_2$—
G = —OCH$_2$—
G = —NHCOCH$_2$CH$_2$CH(NH—FMOC)—
or G = —NHCOCH(NH—FMOC)CH$_2$CH$_2$—

Z = —NH—CH$_2$—
Z = —OCH$_2$—
Z = —NHCOCH$_2$CH$_2$CH(NH$_2$)—
or Z = —NHCOCH(NH$_2$)CH$_2$CH$_2$—

(For an experimental demonstration of the synthesis of anthracycline derivatives using this method see Sections 7.1.17, 7.1.18, 7.1.20, 7.1.21, 7.1.22, and 7.1.23, infra).

Alternatively, acyl derivatives of anthracycline antibiotics containing a reactive amine are synthesized according to the scheme presented below (Scheme 1A) by first reacting an anthracycline antibiotic having a primary or secondary amine group on the sugar moiety with an active ester, mixed anhydride or active chlorine atom of an fluorenylmethyloxycarbonyl (FMOC)-protected amino acid or peptide (herein referred to generally as an "FMOC-NH-peptide-CO-R'" in which R' represents an active ester moiety derived from N-hydroxysuccinimide or N-hydroxybenezotriazole; a mixed carbonic-carboxylic anhydride derived from isobutylchloroformate; or a chlorine atom; and removing the FMOC protecting group to form an acylanthracycline antibiotic derivative. (For an experimental demonstration of 3'amidyl or 3'peptidyl anthracycline derivatives synthesized using this method see Sections 7.1.1–7.1.16 infra).

The amidyl or peptidyl derivative is then reacted with an FMOC-NH-G-COR moiety as defined above to form an FMOC-acyl anthracycline antibiotic derivative containing a reactive amine. The FMOC protecting group is removed under strictly anhydrous, basic conditions to yield an acyl anthracycline antibiotic derivative.

For convenience in Schemes 1 and 1a, the FMOC protecting group is removed using diethylamine (Et$_2$NH) under anhydrous conditions in dimethylformamide. Other agents such as dialkylamine, piperidine, morpholine or ammonia may also be used in Scheme 1 or 1a.

Scheme 1a is presented using ADR but can be used to prepare acyl derivatives of any anthracycline antibiotic having an amine group on the sugar moiety including ADR, DNR, idarubicin, epirubicin, esorubicin, carminomycin, 4-demethoxy-4'-O-methyl doxorubicin, 4'-O-tetrahydropyranyl doxorubicin, etc.

SCHEME 1a

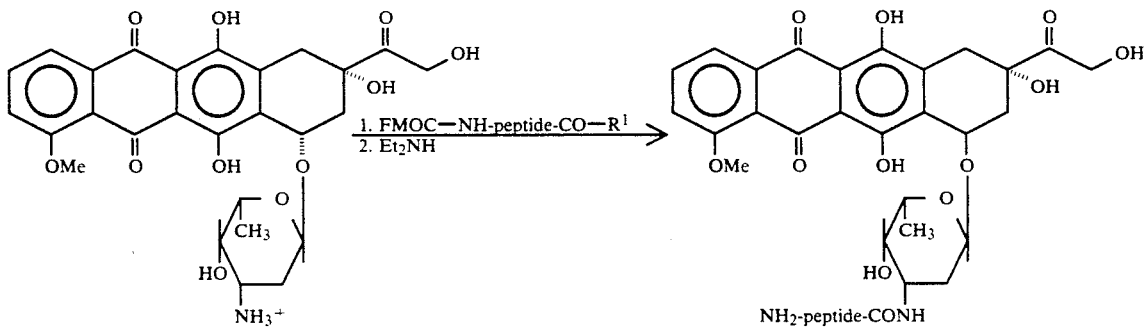

-continued
SCHEME 1a

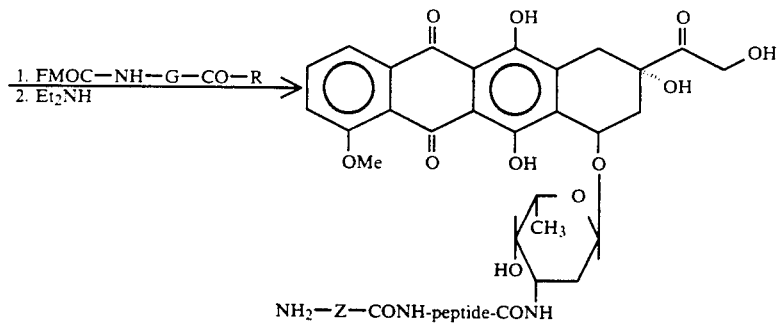

NH$_2$—Z—CONH-peptide-CONH in which

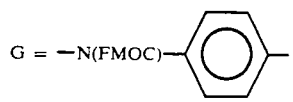 and 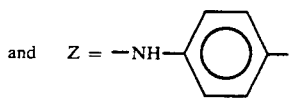

G = —N(FMOC)—CH$_2$—
G = —OCH$_2$—
G = —NHCOCH$_2$CH$_2$CH(NH—FMOC)—
or G = —NHCOCH(NH—FMOC)CH$_2$CH$_2$—

Z = —NH—CH$_2$—
Z = —OCH$_2$—
Z = —NHCOCH$_2$CH$_2$CH(NH$_2$)—
or Z = —NHCOCH(NH$_2$)CH$_2$CH$_2$—

According to another method, acyl derivatives of anthracycline antibiotics containing a reactive amine are synthesized according to the reaction scheme illustrated below (Scheme 2). In Scheme 2, ADR is used for purposes of illustration only. According to Scheme 2, the amine-containing derivatives formed are respectively -hydrazide-succinyl and -hydrazide-glutaric-anthracycline derivatives when n is 2 or 3.

(For an experimental demonstration of an anthracycline antibiotic derivative prepared using this method see Section 7.1.19, infra).

According to yet another method, C-13 hydrazone derivatives of anthracycline antibiotics having a C-13 keto group are synthesized by condensation of the C-13 keto group of an anthracycline antibiotic and an acid hydrazide. According to a preferred method, an acid hydrazide is reacted with the anthracycline antibiotic in

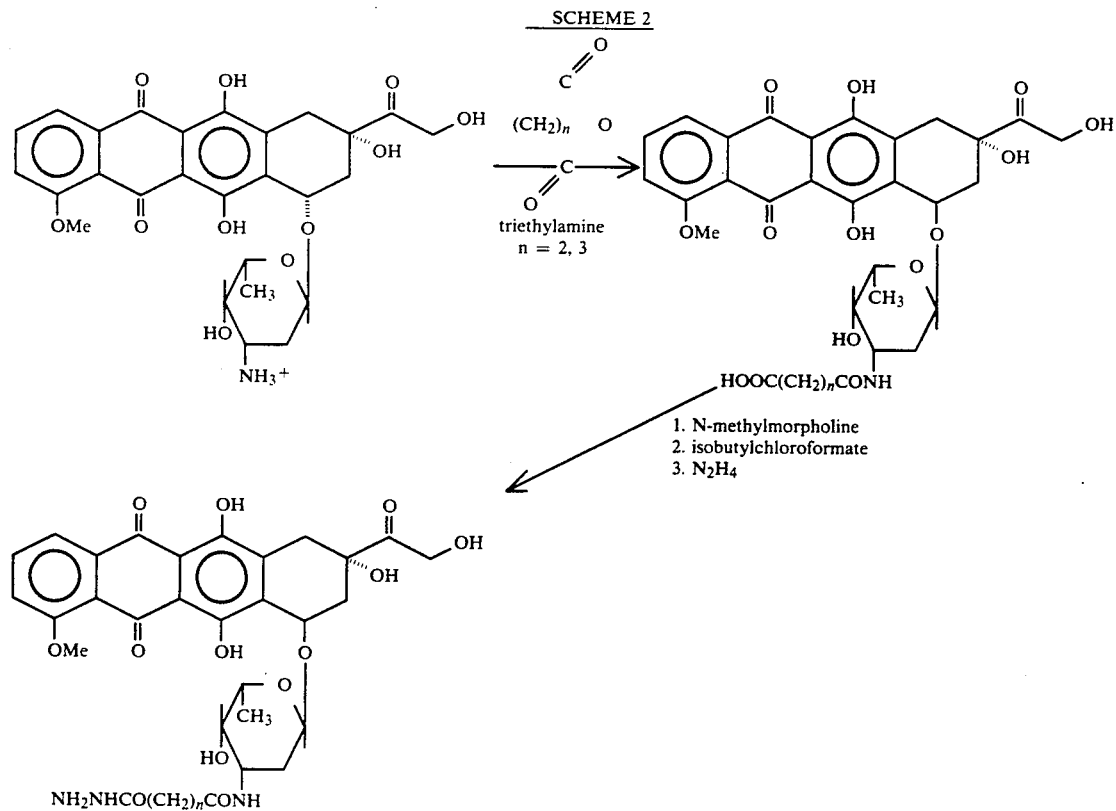

appropriate excess molar amount of hydrazide so that little to no bisanthracycline product is formed. If any bis-product is formed, it is not critical since such product simply will not react when the product(s) is reacted with an aldehyde group of an oxidized carbohydrate moiety of an antibody or antibody fragment to form an antibody conjugate of the invention. This general method is illustrated below in Scheme 3, again using ADR for illustrative purposes only. This method is useful for preparing reactive amine-containing derivatives of anthracycline antibiotics of any anthracycline antibiotics having a C-13 keto group including but not limited to daunorubicin, doxorubicin, epirubicin, esorubicin, idarubicin, carminomycin, 4-demethoxy-4'-O-methyl doxorubicin, 4'-O-tetrahydropyranyl doxorubicin, 3-deamino-3'-(3''-cyano-4''-morpholinyl) doxorubicin, etc.

invention for preparing aqueous soluble site selective antibody conjugates. In this case, a ketone group on the trisaccharide moiety of aclacinomycin is reacted with the acid hydrazide to form the reactive amine-containing anthracycline antibiotic derivative.

According to a variation of the method presented in Scheme 3, a reactive amine-containing derivative of an anthracycline antibiotic is synthesized by reacting an anthracycline antibiotic having a C-13 keto group with an oligoglutamylhydrazide having X glutamyl residues and X+1 hydrazide groups in appropriate molar ratio such that X anthracycline moieties are covalently attached to the oligoglutamylhydrazide polymer, in which X is an integer 1-50; preferably 1-10. (For an experimental demonstration of the synthesis of an anthracycline derivative prepared using this method see Section 7.2.2, infra).

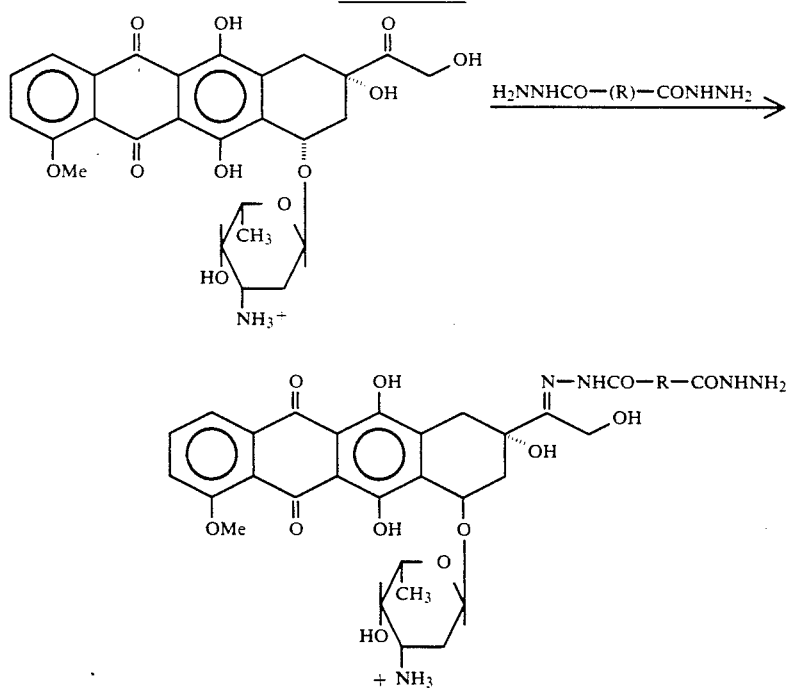

SCHEME 3 where R = alkylene chain with 0-20 carbon atoms in the chain (For an experimental demonstration of the synthesis of an anthracycline derivative using this method see Sections 7.2 1 & 7.2.3, infra).

In addition, it is envisaged that the method depicted in Scheme 3 can be used to prepare hydrazone containing amine derivatives of anthracycline antibiotics such as aclacinomycin which are useful according to present According to yet another method, a reactive amine-containing derivative of an anthracycline antibiotic is synthesized by forming a C-14 methylene thioether or a C-14 tertiary amine linkage according to any of the reaction schemes illustrated below in Schemes 4, 4a and 5.

SCHEME 4

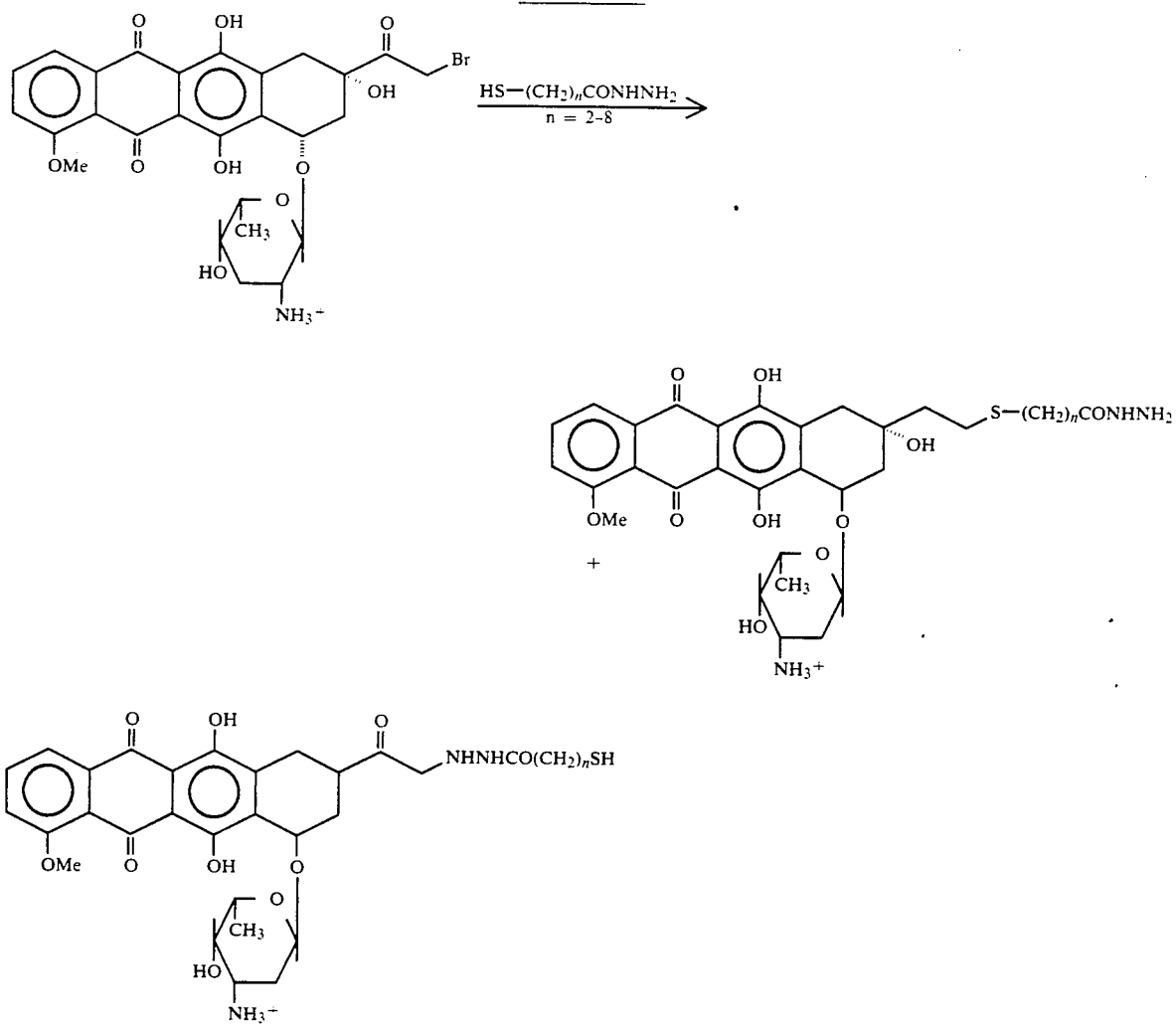

(For an experimental demonstration of the synthesis of an anthracycline derivative using this method see Section 7.3, infra).

As indicated in Scheme 4, using this method both the desired S-alkylation product having a reactive amine and an N-alkylation product which does not have a reactive amine are formed. The mixture of products formed does not really present a problem since only the S-alkylation product will react with an aldehyde moiety of an oxidized carbohydrate moiety of an antibody or antibody fragment to yield an anthracycline antibiotic antibody conjugate according to the invention.

SCHEME 4a

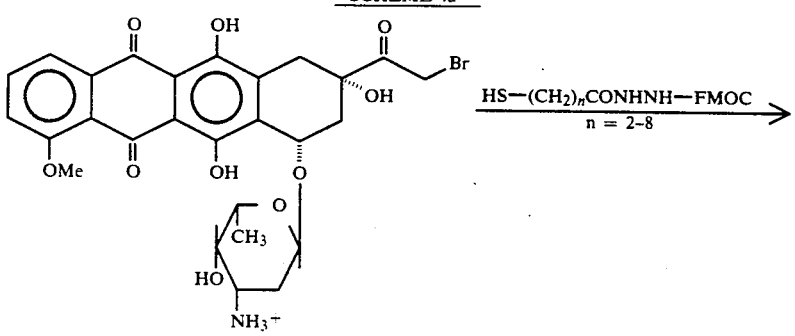

SCHEME 4a

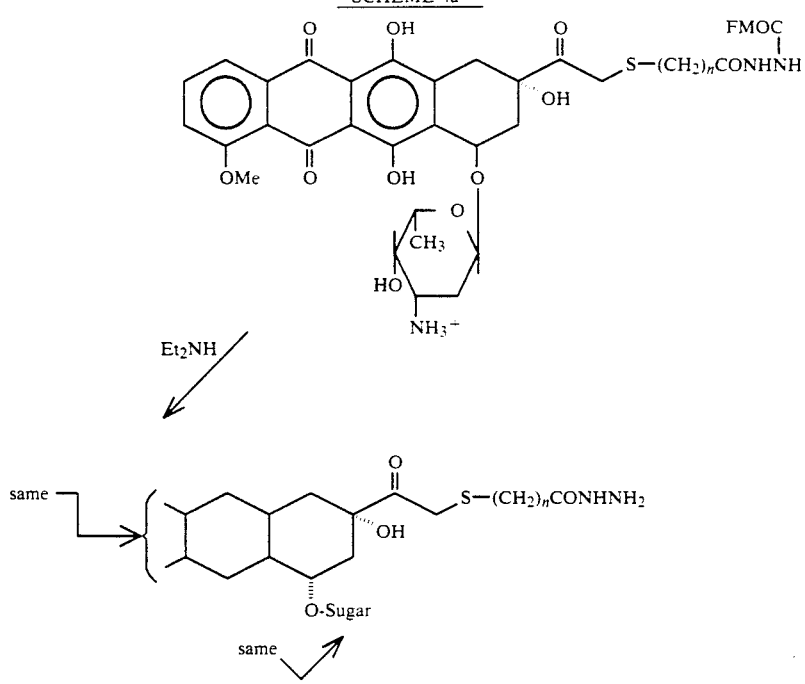

In order to avoid a formation of an N-alkylation product, a C-14 thioether derivative of an anthracycline antibiotic is prepared as illustrated in Scheme 4a above. As an illustrative example, using the method presented in Scheme 4a, DNR-14-S-propionyl hydrazide is prepared by reacting 14-Bromo-DNR with an N-FMOC-3-mercapto-propionyl hydrazide and then removing the FMOC protecting moiety under anhydrous, basic conditions.

As illustrated in Scheme 5, a C-14 tertiary amine moiety can be reacted with 14-bromo-DNR to form an amine-containing derivative which is useful according to the invention to prepare a therapeutic antibody conjugate.

SCHEME 5

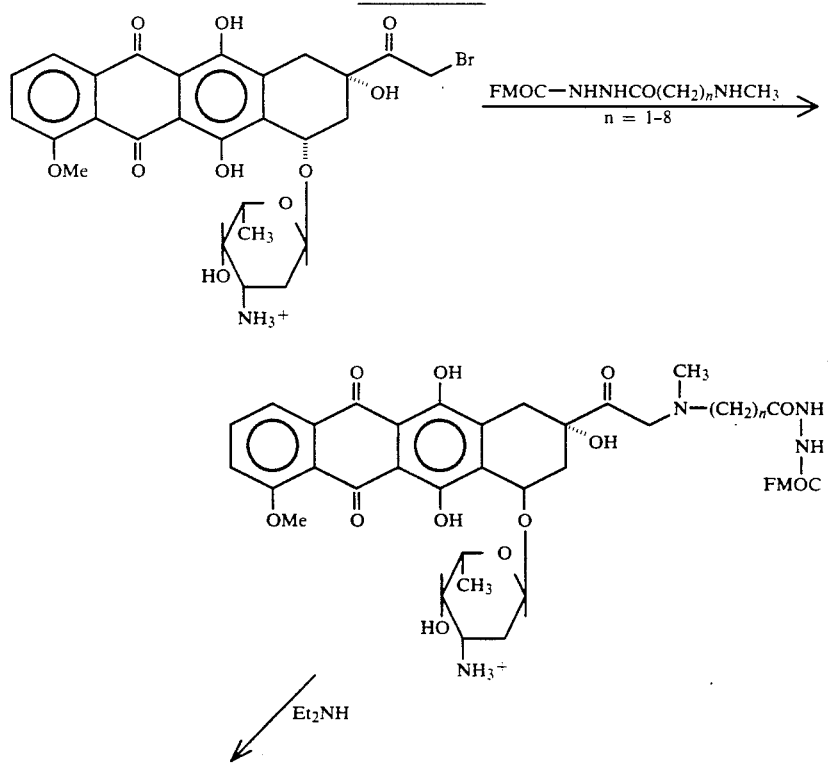

SCHEME 5

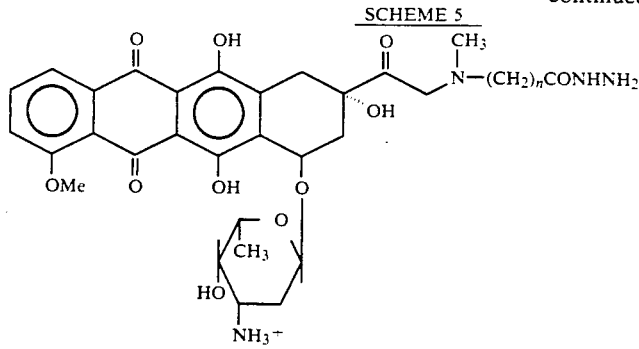

6.3. METHODS FOR PREPARING ANTIBODY CONJUGATES since antibodies are glycoproteins, compounds may be attached to the carbohydrate moiety covalently attached to the peptide backbone of the molecule. Some of the carbohydrate moieties are located on the Fc region of the immunoglobulin and are required for bonding of components of the complement system to occur. The carbohydrate moiety of the Fc region of an immunoglobulin may be utilized in the scheme described herein. Alternatively, the Fab or Fab' fragments of any immunoglobulins which contain carbohydrate moieties may be utilized in the reaction scheme described herein. An example of such an immunoglobulin is the human IgM sequenced by Putnam et al. (1973, Science 182: 287).

As explained in detail below, the carbohydrate side chains of antibodies or antibody fragments may be selectively oxidized to generate aldehydes. The resulting aldehyde may then be reacted with an amine group (e.g., ammonia derivatives such as alkoxyamine, hydrazine, hydrazide, phenylhydrazine, phenylhydrazide, semicarbazide or thiosemicarbazide) to form an oxime, hydrazone, phenylhydrazone, semicarbazone or thiosemicarbazone.

Alternatively, the carbohydrate moiety of the antibody may be modified by enzymatic techniques so as to enable attachment to or reaction with amine groups. For example, neuraminidase plus galactose oxidase may be used to form an aldehyde moiety.

6.3.1. CHEMICAL METHODS OF OXIDATION of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, in Organic Reactions 2, p.341; Bunton, 1965, Oxidation in Organic Chemistry, Vol. 1 Wiberg, ed., Academic Press, New York, p.367.

Oxidation of antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, ten to 100 times as much as the amount of the oxidizable carbohydrate. The optimal amount, however, can be determined by routine experimentation.

In the process for oxidizing antibodies with oxygen acids or salts thereof, the optional ranges include a pH from about 4 to 8, a temperature of from 0° to 37° C., and a reaction period of from about 15 minutes to 12 hours.

During the oxidation of the glycoprotein with an oxygen acid or a salt thereof, light is preferably excluded to prevent over oxidation of the glycoprotein.

6.3.2. ENZYMATIC METHOD OF OXIDATION

Oxidation of the carbohydrate portion of antibody molecules may also be accomplished using the enzyme galactose oxidase (Cooper et al., 1959, J. Biol. Chem. 234: 445) with or without neuraminidase. The antibody is used in aqueous solution, the concentration being generally 0.5 to 20 mg/ml. The enzyme generally is used at pH about 5.5 to about 8.0. The influence of pH, substrate concentration, buffers and buffer concentrations on enzyme reaction are reported in Cooper et al., supra. Such enzymatic oxidation probably would not be useful when the antibody employed is an IgG molecule.

6.3.3. COUPLING OXIDIZED ANTIBODY AND AN ANTINEOPLASTIC AMINE DERIVATIVE OF AN ANTHRACYCLINE ANTIBIOTIC

The antibody conjugates of the invention are produced by reacting an oxidized antibody with an anthracycline antibiotic having an available amine group selected from the group consisting of hydrazine, hydrazide, phenylhydrazine, phenylhydrazide, alkoxyamine, phenoxyamine, semicarbazide and thiosemicarbazide groups. High mannose containing antibodies can also be used to form conjugates with anthracycline antibiotics (reviewed in detail in patent application Ser. No. 153,175, filed Feb. 8, 1988, now abandoned, incorporated herein by reference. The immediately resulting products contain a carbon-nitrogen double bond resulting from elimination of a molecule of water from the initial addition products:

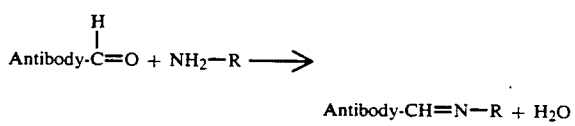

Antibody-CH=N—R + H$_2$O

For a general discussion of the reaction of aldehydes with hydrazine derivatives, see March, 1978, in Advanced Organic Chemistry: Reactions Mechanisms and Structure, McGraw Hill Co., New York, pp. 824–825.

A solution of the oxidized antibody at a concentration from about 0.5 to 20 mg/ml is mixed with an amine derivative of an anthracycline antibiotic (molar ratios of reactive amine group to antibody aldehyde ranging from about 1 to about 10,000) and the solution incubated for from about 1 to 18 hours, preferably in the dark. Suitable temperatures are from 0° to 37° C. and pH may be from about 6 to 8.

6.3.4. REMOVAL OF AGGREGATES AND NON-COVALENTLY BOUND ANTHRACYCLINE ANTIBIOTIC

The resulting antibody conjugates may contain aggregates formed by intramolecular Schiff base formation between primary amines of amino acids and the aldehyde moieties of the antibody molecule. Additionally, amine derivatives of anthracycline antibiotics show strong non-covalent binding to antibodies having an oxidized carbohydrate moiety as well as moderate binding to unmodified antibodies.

Thus in these instances, any aggregates formed and any non-covalently bound anthracycline antibiotic are optionally removed from the desired antibody conjugates by suitable gel filtration methods including but not limited to high performance gel permeation liquid chromatography.

Removal of undesirable aggregates is particularly important because the antibody conjugates are used in vivo to deliver the attached therapeutic anthracycline antibiotic to a desired target site. Any such antibody aggregates would be taken up by the reticuloendothelial system for removal, and such transport away from the target site or specific tissue would diminish the degree of localization and hence therapeutic effectiveness of the conjugates administered as well as potentially leading to toxic effects on non-target sites.

6.4. USES OF AMINE DERIVATIVES OF ANTHRACYCLINE ANTIBIOTICS AND ANTIBODY CONJUGATES

The amine derivatives of anthracycline antibiotics of the present invention are particularly well suited for use in the preparation of therapeutic antibody conjugates. Thus, these derivatives represent intermediates in the preparation of therapeutic antibody-anthracycline antibiotics conjugates. Selective attachment of an amine derivative of an anthracycline antibiotic via a reactive amine group to an oxidized carbohydrate moiety of an antibody or antibody fragment results in a therapeutically effective aqueous soluble conjugate that retains the antibody immunospecificity.

Such antibody conjugates are particularly advantageous for in vivo therapy because they are preferentially delivered to the target site and should avoid cardiotoxicity which is a major limiting problem for use of anthracycline antibiotics.

Antibodies used in the present invention may be conventional antibodies or monoclonal antibodies. Use of monoclonal antibodies offers several advantages because each monoclonal antibody is specific for one antigenic determinant and large amounts can easily be produced using known techniques.

Antibodies useful in the invention are directed against any target associated with cellular disorders which can be treated using an antineoplastic anthracycline antibiotic. The term "cellular disorders" as used throughout this application is intended to encompass neoplasms and other hyperplastic conditions which are amenable to treatment using antineoplastic anthracycline antibiotics. Such cellular disorders include but are not limited to: acute lymphocytic leukemia, acute granulocytic leukemia, acute monolymphoblastic leukemia, malignant lymphomas including, but not limited to non-Hodgkin's lymphomas, carcinomas including but not limited to carcinoma of the breast, small (oat)-cell carcinoma, carcinoma of the bladder, bronchiogenic carcinoma, carcinomas of the endometrium, testes, prostate, cervix and head and neck; sarcomas including but not limited to osteogenic sarcoma, Ewing's sarcoma, and soft-tissue sarcomas, metastatic adenocarcinoma of the breast, metastatic thyroid carcinoma and plasma cell myeloma.

In addition, the term "cellular disorders" is further intended to encompass any neoplastic tumorous growth which is amenable to therapeutic treatment using the antibody conjugates of amine derivatives of anthracycline antibiotics as determined by the following in vivo test.

A small sample of a tumor to be treated is obtained by conventional methods and divided into several aliquots. An antibody, either monoclonal or polyclonal, immunoreactive with an immunospecificity for the particular tumor is identified and/or prepared using conventional or hybridoma techniques. An antibody-anthracycline antibiotic conjugate is prepared according to the present invention (see Section 6.3, above). One aliquot of the tumor sample is inserted subcapsularly into the kidney of an experimental animal. Either a normal or nude mouse affords a convenient experimental animal model. The tumor fragment is measured, in situ, using an ocular micrometer and the antibody-anthracycline/antibiotic conjugate is administered intravenously for several days. Animals having a similarly implanted subrenal capsule tumor fragment but which are untreated serve as negative controls. Measurements are made, either periodically of the implanted tumor tissue using a group of animals or at a given time period following implementation, and inhibition of tumor growth or reduction in tumor size of the treated animals indicates therapeutic effectiveness of the conjugates. Using the above scheme, any human tumor tissue can be screened for in vivo sensitivity to the antibody-anthracycline antibiotic conjugates of the invention.

Examples of targets associated with cellular disorders which can effectively be treated using the antibody conjugates of the invention include but are not limited to: tumor antigens, histocompatibility, differentiation and other cell membrane antigens, enzymes, hormone receptors, oncogene products, etc. Additionally a combination of antibodies reactive to different antigenic determinants may be used. Immunoglobulins which may be used as carriers include: certain classes of antibodies such as IgA, IgD, IgE, IgM; certain classes of IgG; or certain fragments of immunoglobulins, e.g., half antibody molecules (or single heavy: light chain pair), Fab, Fab' of (Fab')$_2$ fragments.

Alternate possibilities including therapeutic activity without release from the conjugate, enzymatically catalyzed release, and chemically induced release at an in vivo target are offered to explain the therapeutic effectiveness of the anthracycline antibiotic antibody conjugates of the invention in vivo. The invention, however, is not to be limited to any particular theory or mechanism for such therapeutic effectiveness.

The antibody conjugates of the invention are ideally suited for use in methods of in vivo therapeutic treatment of cellular disorders. Such methods comprise administering a therapeutically effective amount of an antibody-anthracycline antibiotic conjugate of the invention, said conjugate being immunoreactive with and immunospecific for a target site associated with said cellular disorder and substantially non-immunoreactive with and non-immunospecific for tissue not associated with said cellular disorder. The conjugates of the invention are therapeutically effective for treating cellular disorders amenable to treatment with the anthracycline antibiotic precursors from which the conjugates are derived.

Additionally, it is envisaged that the antibody-anthracycline antibiotic conjugates may be useful for treatment of tumors which are resistant to the free anthracycline antibiotic precursor from which the amine derivative is derived. To determine whether a particular tumor may be therapeutically treated in vivo using a specific antibody-anthracycline antibiotic conjugate, the in vivo test described above is utilized.

In vivo administration may involve use of pharmaceutical compositions of the antibody-anthracycline antibiotic conjugates in any suitable carrier, including serum or physiological saline, with or without another protein such as human serum albumin. Dosages of the conjugates may be readily determined by one of ordinary skill and may differ depending upon the nature of the cellular disorder and the particular anthracycline antibiotic employed. The preferred mode of administration is generally parenteral via intramuscular, intravenous, intraarterial, intrathecal, intraperitoneal and intralymphatic routes.

The following series of Examples are presented for purposes of illustration and not by way of limitation on the scope of the invention.

7. SYNTHESIS OF AMINE-CONTAINING DERIVATIVES OF DOXORUBICIN OR ADRIAMYCIN (ADR)

7.1. 3' ACYL-ADR DERIVATIVES

In the following examples, FMOC-protected 3' acyl-ADR derivatives were prepared as described in Section 6.2. If thin layer chromatography [chloroform/methanol 8:2 (silica); acetonitrile/0.1% trifluoroacetic acid (TFA) 1:1 (reverse phase)] indicated that the resulting product was impure, the product was purified, for example, by flash chromatography on silica gel (230-400 mesh) using a chloroform/methanol mixture.

7.1.1. GLYCYL-ADR(1)

FMOC-gly (1.0 equivalent) was dissolved in dry, nitrogen-bubbled dimethylformamide (DMF) under nitrogen and cooled to 0° C. N-Methylmorpholine (1.0 equivalent) was added; the mixture incubated for about 5 minutes and isobutylchloroformate (1.0 equivalent) was added with stirring. After an additional 3-5 minutes incubation, adriamycin-hydrochloride (ADR-Cl) (0.9-1.0 equivalent) was added along with an equivalent amount of N-methylmorpholine suspended in DMF. The reaction mixture was incubated for 1-2 hours at 0° C., then at about 4° C. for 12-16 hours with stirring. Solvents were removed by rotary evaporation at 30°-35° C. The residue was taken up in ethyl acetate and washed successively with saturated aqueous sodium bicarbonate, 5% aqueous citric or acetic acid and water. The organic layer was dried over sodium sulfate, concentrated by rotary evaporation, and either recrystallized from methanol/ether or precipitated with ether. Yield of FMOC-gly was 75%; melting point: 154°-157° C.; Rf: 0.92 [chloroform/methanol 8:2 (silica)]; Rf: 0.42 [acetonitrile/0.1% aqueous TFA 1:1 (reverse phase)]. Elemental analysis for $C_{44}H_{42}N_2O_{14}.2.5$ $H_2O$; calculated; C, 60.89; H, 5.46; observed: C, 60.96; H, 5.48.

In order to form gly-ADR, FMOC-gly-ADR was dissolved in freshly nitrogen-bubbled DMF (about 10 mg/ml) and cooled to 0° C. Distilled diethylamine was added under nitrogen atmosphere to a final concentration of about 10% via a dried glass syringe. After 15-30 minutes incubation, the amine was evaporated under a vigorous stream of nitrogen. Solvents were removed by rotary evaporation at 35° C. The residue was stored overnight in ether at 0° C. After the ether was removed, e.g., by decantation, the residue was dissolved in 5% acetic acid and extracted with ether until no further red color appeared in the organic layer. The aqueous layer was lyophilized. Yield of gly-ADR (1).HOAc was 53 mg (72%). The melting point of (1) was 209° C. (dec.) Rf: 0.05 [chloroform/methanol 8:2 (silica)]; Rf: 0.35 [acetonitrile 0.1% aqueous TFA 1:1 (reverse phase)]. Elemental analysis for $C_{31}H_{36}N_2O_{14}.0.5$ $H_2O$ calculated: C, 55.60; H, 5.57; N, 4.20; observed C, 55.78; H, 5.52; N, 4.63.

7.1.2. ALANYL-ADR (2)

Alanyl-ADR (2) (ala-ADR) was prepared as described above for gly-ADR, except that FMOC-ala was used as the initial starting material. Yield of FMOC-ala-ADR was 97%; melting point was 118°-120° C.; Rf: 0.94 [chloroform/methanol 8:2 (silica); Rf: 0.79 [acetonitrile/0.1% aqueous TFA 1:1 (reverse phase)]. Elemental analysis of the FMOC-ala-ADR $C_{45}H_{44}N_2O_{14}.H_2O$; calculated: C, 63.22; H, 5.42; N, 3.27; observed C, 63.18; H, 5.39; N, 3.25.

Yield of (2) .HOAc was 560 mg (79%). The melting point of (2) was 170° C. (decomp.) Rf: 0.24 [chloroform/methanol 8:2 (silica)]; Rf: 0.21 [acetonitrile 0.1% aqueous TFA 1:1 (reverse phase)]. Elemental analysis for $C_{32}H_{38}N_2O_{14}.2.0$ $H_2O$, calculated; C, 4.08: H, 5.96: N, 3.94: observed: C, 53.95: H, 5.89: N, 3.95.

7.1.3. D-ALA-ADR(3)

D-alanyl-ADR (3) (D-ala-ADR) was prepared as described above for gly-ADR except that FMOC-D-ala was used as the initial starting material. Yield of FMOC-D-ala-ADR was 172 mg (64%); melting point was 170° C. (decomp.); Rf: 0.36 (silica, chloroform/methanol/acetic acid, 90:5:5). Elemental analysis for $C_{45}H_{44}N_2O_{14}.4.5$ $H_2O$, calculated: C, 58.88; H, 5.82; N, 3.07; observed: C, 59.02; H, 5.46; N, 2.81.

Yield of (3).HOAc was 73 mg (72%). The melting point of (3) was 204° C. (decomp.). Rf: 0.56 (silica, chloroform/methanol/$H_2O$, 20:10:1). Elemental analysis for $C_{32}H_{38}N_2O_{14}.1.5$ $H_2O$, calculated: C, 54.78; H, 5.89; N, 4.01; observed: C, 54.96; H, 5.83; N, 4.49.

7.1.4. ISOLEUCINYL-ADR (4)

FMOC-ile (1.0 equivalent) and N-hydroxysuccinimide (1.1 equivalent) were dissolved in DMF/$CH_2Cl_2$ under nitrogen and cooled to −5° C. Dicyclohexylcarbodiimede (DCC) (0.5M in methylene chloride, 1.0–1.1 equivalent) was added and the mixture was stirred at 0° C. for 1 hour, then at room temperature for 18 hours. White precipitate was filtered, and to the filtrate was then added a mixture of ADR (1.0 equivalent) and N-methylmorpholine (1.1 equivalent) in DMF. Stirring was maintained for 7 days at room temperature. Solvents were then removed by rotary-evaporation, leaving a crude product which was redissolved in ethyl acetate and extracted sequentially with 10% acetic acid, water, saturated sodium bicarbonate solution, and water. The organic layer was dried over sodium sulfate, concentrated by rotary evaporation, and either crystallized from methanol/ether or precipitated with ether. The product was dried in vacuo. Yield of FMOC-ile-ADR was 33%; melting point was 147° C. (decomp); Rf: 0.45 [chloroform/methanol/acetic acid 90:5:5 (silica);]; Rf: 0.25 [chloroform/methanol 95:5 (silica)]. Elemental analysis for $C_{48}H_{50}N_2O_{14} \cdot H_2O$, calculated: C, 64.28; H, 5.84; N, 3.12; observed: C, 63.98; H, 5.81; N, 3.11.

The FMOC moiety was removed from FMOC-ile-ADR to yield ile-ADR (4) as described for gly-ADR (1). Yield of (4).HOAc was 48%. The melting point of (4) was 192° C. (decomp). Elemental analysis for $C_{35}H_{45}N_2O_{14} \cdot H_2O$, calculated: C, 57.14; H, 6.44; N, 3.81; observed: C, 57.47; H, 6.12; N, 3.84.

7.1.5. VALYL-ADR (5)

Valyl-ADR (5) was prepared as described above for ile-ADR except that FMOC-val was used as the initial starting material. Yield of FMOC-val-ADR was 35%; melting point was 154° C. (decomp.); Rf: 0.46 [chloroform/methanol/acetic acid 95:5:5 (silica)]; Rf: 0.71 [chloroform/methanol 9:1 silica)]. Elemental analysis for $C_{47}H_{48}N_2O_{14} \cdot 2.5\ H_2O$, calculated: C, 62.04; H, 5.87; N, 3.08; observed: C, 61.99; H, 5.70; N. 3.12.

Yield of (5).HOAc was 90%. The melting point of (5) was 197° C. (decomp.). Elemental analysis for $C_{34}H_{42}N_2O_{14}$ calculated: C, 58.11; H, 6.02; N, 3.99; observed: C, 58.10; H, 6.07; N, 4.04.

7.1.6. TYROSINYL-ADR (6)

Tyrosinyl-ADR (tyr-ADR) (6) was prepared as described above for gly-ADR, except that FMOC-tyr was used as the initial starting material. Yield of FMOC tyrosinyl-ADR was 82%; melting point 180°-182° C. (decomp.); Rf: 0.91 [chloroform/methanol 8:2 (silica). Elemental analysis of the FMOC-ADR $C_{51}H_{48}N_2O_{15} \cdot 1.5\ H_2O$; calculated: C, 64.08; H, 5.38; N, 2.94; observed: C, 64.17; H, 5.56; N, 3.47.

Yield of (6).HOAc was 140 mg (86%). The melting point of (6) was 200° C. (dec.) Rf: 0.58 [chloroform/methanol 8:2 (silica)]; Rf: 0.53 [acetonitrile 0.1% aqueous TFA 1:1 (reverse phase)]. Elemental analysis for $C_{38}H_{42}N_2O_{15} \cdot 0.5\ H_2O$; calculated: C, 58.83; H. 5.59; N, 3.63; observed: C, 58.67, H. 5.82; N, 4.29.

7.1.7. ARGINYL-ADR (7)

Arginyl-ADR (7) (arg-ADR) was prepared as described for gly-ADR with the following exceptions: (a) FMOC-arg was the initial starting material; and (b) once the reaction was complete, the crude product mixture was concentrated by rotary evaporation and purified by preparative HPLC on a Rainin C-18 Dynamax column (21.4 mm×25 cm) using gradient elution (solvent A: 0.1% aqueous TFA; solvent B: acetonitrile) at 15 ml/minute. A non-linear 38 minute gradient was developed. The detector was set at 300 nm; product peaks collected and pooled; and the FMOC-arg-ADR obtained was concentrated by rotary evaporation and lyophilization. Yield of FMOC-arg-ADR was 80%; melting point 150 C; Rf: 0.40 [n-butanol/acetic acid/water 3:1:1 (silica)]; Rf: 0.23 [acetonitrile/0.1% aqueous TFA 1:1 (reverse phase)]. Elemental analysis for $C_{49}H_{51}N_5O_{16} \cdot 2\ H_2O$; calculated: 55.57; H, 5.23; N, 6.64; observed: C, 55.64; H, 5.24; N, 6.73.

The FMOC-protecting group was removed from the FMOC-arg-ADR as described above. The yield of arg-ADR (6).2HOAc was 173 mg (70%). The melting point of (7) was 214° C. (decomp.) Rf: 0.06 [chloroform/methanol 8:2 (silica)]; Rf: 0.15 [acetonitrile 0.1% aqueous TFA 1:1 (reverse phase)].

7.1.8. ALANYL-ALANYL-ADR (8)

Alanyl-alanyl-ADR (8) was prepared as described above for ile-ADR except that FMOC-ala-ala was used as the initial starting material. Yield of FMOC-ala-ala-ADR was 203 mg (57%), melting point was 165°-169° C. (decomp); Rf: 0.43 (silica, chloroform/methanol 9:1), 0.23 (silica, chloroform/methanol/acetic acid 90:5:5. Elemental analysis for $C_{48}H_{49}N_3O_{15} \cdot 0.5\ H_2O$, calculated: C, 62.87; H, 5.50; N, 4.60; observed: C, 62.94; H, 6.06; N, 4.56.

Yield of (8).HOAc was 100 mg (84%). The melting point of (8) was 197° C. (decomp.) Rf: 0.30 (silica, chloroform/methanol/acetic acid 20:10:1). Elemental analysis for $C_{35}H_{43}N_3O_{15}$, calculated: C, 56.37; H, 5.81; N, 5.66; observed: C, 56.21; H, 5.84; N, 5.50.

7.1.9. ALANYL-ALANYL-ALANYL-ADR (9)

Alanyl-alanyl-alanyl-ADR (9) was prepared as described above for ile-ADR except that FMOC-ala-ala-ala was used as the initial starting material. Yield of FMOC-ala-ala-ala-ADR was 158 mg (37%); melting point was 178°-182° C.; Rf: 0.65 (silica, chloroform/methanol 9:1), 0.18 (silica, chloroform/methanol/acetic acid 90:5:5). Elemental analysis for $C_{51}H_{54}N_4O_{16} \cdot 0.5\ H_2O$, calculated: C, 61.99; H, 5.61; N, 5.70; observed: C, 61.73; H, 5.97; N, 5.66.

Yield of (9).HOAc was 80 mg (89%). The melting point of (9) was 223° C. (decomp). Rf: 0.27 (silica, chloroform/methanol/acetic acid 20:10:1). Elemental analysis for $C_{38}H_{48}N_4O_{16} \cdot 1.5\ H_2O$, calculated: C, 54.08; H, 6.09; N, 6.67; observed: C, 54.09; H, 5.97; N, 6.54.

7.1.10. D-ALANYL-ALANYL-ALANYL-ADR (10)

D-Alanyl-alanyl-alanyl-ADR (10) was prepared as described above for ile-ADR except that FMOC-D-ala-ala-ala-ala was used as the initial starting material. Yield of FMOC-D-ala-ala-ala-ADR was 196 mg (61%); melting point was 195°-199° C.; Rf: 0.32 (silica, chloroform/methanol/acetic acid 85:10:5). Elemental analysis for $C_{51}H_{54}N_4O_{16} \cdot 1.5\ H_2O$, calculated: C, 60.88; H, 5.71; N, 5.59; observed: C, 60.96; H, 5.92; N, 5.64.

Yield of (10).HOAc was 65 mg (80%). The melting point of (10) was 201°-203° C. (decomp.). Rf: 0.40 (silica, chloroform/methanol/acetic acid 20:10:1). Elemental analysis for $C_{38}H_{48}N_4O_{16} \cdot 1.0\ H_2O$, calculated: C, 54.66; H, 6.04; N, 6.74; observed: C, 54.44; H, 5.99; N, 6.84.

7.1.11. TYR-GLY-GLY-ADR (11)

FMOC-Tyr-Gly-Gly

FMOC-Tyr-Gly-Gly was initially prepared as follows:

Tyr-gly-gly (5.0 gm, 16.9 mMole) and sodium bicarbonate (1.42 gm, 16.9 mMole) were suspended in 20 ml water, and to this was added 9-fluorenylmethyl succinimidyl carbonate (6.27 gm, 1.86 mMole) dissolved in 30 ml dioxane. The reaction mixture was stirred for 1.5 hours, poured into 1 liter 2% sodium bicarbonate, and extracted with ether (2×250 ml). The aqueous layer was acidified to pH 2 with concentrated HCl at 0° C., precipitating a white solid. The solid was filtered, washed with water and ether, and air dried. Two recystallizations from methanol yielded pure FMOC tyr-gly-gly. Yield: 4.70 gm, (53.8%); melting point, 215°–216° C.; Rf: 0.33 [chloroform/acetic acid/methanol 85:5:10 (silica)]. Elemental analysis for $C_{28}H_{27}N_3O_7$; calculated: C, 64.98; H, 5.26; N, 8.12; observed: C, 64.76; H, 5.32; N, 8.07.

FMOC-Tyr-gly-gly was coupled to ADR as in Section 7.1.1. for gly-ADR. Yield of FMOC-tyr-gly-gly-ADR was 95%; melting point 150°–153° C.; Rf: 0.63 [chloroform/methanol 8:2 (silica); Rf: 0.68 [acetonitrile/0.1% aqueous TFA 1:1 (reverse phase)]. Elemental analysis for $C_{55}H_{54}N_4O_{17}.H_2O$; calculated: C, 62.25; H, 5.32; N, 5.30; observed: C, 62.17; H, 5.92; N, 5.09. The protecting FMOC moiety removed from the product as described in Section 7.1.1. for gly-ADR. Yield of the product tyr-gly-gly-ADR.HOAc was 68 mg (80%); melting point, 165° C. (decomp.); Rf: 0.10 [chloroform/methanol 8:2 (silica)]; Rf: 0.53 [acetonitrile 0.1% aqueous TFA 1:1 (reverse phase)]. Elemental analysis for $C_{42}H_{48}N_4O_{17}.2\ H_2O$; calculated: C, 55.01; H, 5.72; observed: C, 55.15; H, 5.54.

7.1.12. TYR-GLY-GLY-ARG-ADR (12)

FMOC-Tyr-Gly-Gly (26 mg, 0.050 mMole) was activated as described in Section 7.1.1. for FMOC-gly. The FMOC-tyr-gly-gly was then coupled to arg-ADR. In practice, arg-ADR.2 HOAc prepared as described in Section 7.1.4 (41 mg, 0.050 mMole) and N-methylmorpholine were reacted with activated FMOC-tyr-gly-gly in DMF. After 18 hours reaction time, solvents were removed by rotary evaporation and crude FMOC-tyr-gly-gly-arg-ADR was isolated by trituration with ether. The solid was filtered and air dried to yield 58 mg (92%); Rf: 0.36 [n-butanol/acetic acid/water 4:1:1 (silica)].

The FMOC moiety of FMOC-tyr-gly-gly-arg-ADR was removed to yield tyr-gly-gly-arg-ADR (12). Yield of (12).2HOAc was 36 mg (84%); melting point 204° C. (dec.) Rf: 0.06 [chloroform/methanol 8:2 (silica)]; Rf: 0.15 [acetonitrile 0.1% aqueous TFA 1:1 (reverse phase)]. Elemental analysis for $C_{47}H_{61}N_8O_{18}.2.5\ H_2O$; calculated: C, 52.11; H, 6.07; observed: C, 51.72; H. 5.64.

7.1.13. TYR-ALA-ALA-ALA-ADR (13)

CBZ-Ala-Ala-Ala-t-Butyl Ester

CBZ-ala-ala (10.0 gm, 34.0 mMole) was dissolved in 150 ml tetrahydrofuran (THF) at 0° C. under nitrogen. N-Methylmorpholine (4.18 ml, 38 mMole) was added, followed five minutes later by isobutylchloroformate (4.94 ml, 38 mMole). After an additional five minutes, a previously prepared mixture of ala-O-t-butyl-HCl (6.76 gm, 38 mMole) plus N-methylmorpholine (4.18 ml, 38 mMole) in THF was added. The reaction mixture was incubated with stirring for three days at 4° C. The reaction mixture was then filtered; the filtrate concentrated to a solid by rotary evaporation. The solid was taken up in ethyl acetate and extracted with 5% citric acid (3X), water (2X), saturated aqueous sodium bicarbonate (3X), and water (2X). The organic layer was dried over sodium sulfate, then concentrated by rotary evaporation to a solid and dried in vacuo to yield CBZ-ala-ala-ala-O-t-Butyl ester. Yield: 10.3 gm (78%); Rf: 0.94 [chloroform/acetic acid/methanol 85:5:10 (silica)].

Ala-Ala-Ala-t-Butyl Ester

CBZ-ala-ala-ala-O-t-Butyl (10.0 gm, 25 mMole) was hydrogenated at 47 psi in 300 ml methanol with 5% acetic acid and 700 mg 5% Pd/C catalyst for 1.5 hours. Catalyst was removed by filtration, and the filtrate concentrated by rotary evaporation to an oil. Trituration with ether formed a solid which was filtered and dried in vacuo giving ala-ala-ala-O-t-Butyl.HOAc. Yield: 7.2 gm (88%); Rf: 0.10 [chloroform/acetic acid/methanol 85:5:10 (silica)].

FMOC-(O-t-Butyl) Tyr-Ala-Ala-Ala-t-Butyl Ester

FMOC-(O-t-Butyl) tyr (1.53 gm, 3.3 mMole) was dissolved in 25 ml THF at 0° C. under nitrogen. N-Methylmorpholine (363 ul, 3.3 mMole) was added with stirring, followed five minutes later by isobutylchloroformate (429 ul, 3.3 mMole). The white precipitate which was formed was filtered after 5 minutes and the filtrate added directly to a solution of ala-ala-ala-O-t-Butyl (1.0 gm, 3.0 mMole) and N-methylmorpholine (330 ul, 3.0 mMole) in 30 ml THF at 0° C. The reaction mixture was incubated with stirring overnight at 4° C. Solvents were removed by rotary evaporation. The residue was dissolved in ethyl acetate and extracted with 10% aqueous acetic acid (1X), water (2X), saturated sodium biocarbonate (3X), water (2X), 5% sodium carbonate (3X), and water (2X). After drying over sodium sulfate. The organic layer was evaporated to dryness and crystallized from methanol ether. The product was dried in vacuo over $P_2O_5$ at 60° C. Yield: 5.97 gm, (55%); melting point, 189°–190° C. (main crop); 191°–192° C. (second crop from mother liquor); Rf: 0.81 chloroform/methanol 9:1 (silica)]. Elemental analysis $C_{41}H_{52}N_4O_8$; calculated: C, 67.54; H, 7.19; observed: C, 67.45; H, 7.23.

FMOC-Tyr-Ala-Ala-Ala

FMOC-(O-t-Butyl) tyr-ala-ala-ala-O-t-Butyl (957 mg, 1.32 mMole) was dissolved in 120 ml TFA and stirred for 90 minutes at room temperature. TFA was removed by rotary evaporation and the residue treated with petroleum ether. A white solid formed, which was filtered, washed with petroleum ether, and dried in vacuo. Yield: 776 mg (95%); melting point, 196° C. (decomp.); Rf: 0.53 [Methylene chloride/methanol 9:1 (silica)]. Elemental analysis for $C_{33}H_{36}N_4O_8.0.5\ H_2O$; calculated C, 63.33; H, 5.96; observed C, 67.07; H, 5.95.

FMOC-Tyr-ala-ala-ala was coupled to ADR using ADR-HCl as described above in Section 7.1.1 for FMOC-gly-ADR. Yield of FMOC-tyr-ala-ala-ala-ADR was 47%; melting point was 210°–212° C.; Rf: 0.79 [chloroform/methanol 8:2 (silica)]. Elemental analysis for FMOC-tyr-ala-ala-ala-ADR $C_{60}H_{63}N_5O_{18}$. 1.0 $H_2O$; calculated: C, 62.11; H, 5.65; N, 6.06; observed: C, 62.15; H, 5.81; N, 6.17.

The FMOC moiety was removed as described above to yield tyr-ala-ala-ala-ADR (13).HOAc. Yield of final deprotected product: 65 mg (76%); melting point, 168°–170° C.; Rf: 0.43 [chloroform/methanol 8:2 (silica)]; Rf:0.58 [acetonitrile 0.1% aqueous TFA 1:1 (reverse phase)]. Elemental analysis for $C_{47}H_{57}N_5O_{18}.4.5\ H_2O$; calculated: C, 53.20; H, 6.27; N, 6.63; observed C, 53.01; H, 5.98; N, 6.91.

7.1.14. TYR-VAL-LEU-LYS-ADR (14)

FMOC-(O-t-Butyl) Tyr-Val-Benzyl Ester

FMOC-(O-t-Butyl) Tyr (8.0 gm, 17.4 mMole) was dissolved in 100 ml THF at −10° C. under nitrogen. N-Methylmorpholine (1.9 ml, 17.4 mMole) was added, followed 5 minutes later by isobutylchloroformate (2.25 ml, 17.4 mMole). After an additional 15 minutes, val-benzyl ester-p-tosylate (6.6 gm, 17.4 mMole) and N-methylmorpholine (1.9 ml, 17.4 mMole) were added in 50 ml THF. The reaction mixture was incubated with stirring for 1 hour at −10° C., followed by 18 hours at room temperature. Solvents were removed by rotary evaporation to an oil, which was dissolved in ethyl acetate and extracted with saturated aqueous sodium bicarbonate (2X), 5% citric acid (3X), and water (2X). The organic layer was dried over sodium sulfate and concentrated by rotary evaporation. The oil that remained was then dissolved in chloroform and passed twice through silica gel to remove unreacted FMOC-(O-t-Butyl)tyr. The first elution was accomplished on a 30 ml column with chloroform and increasing amounts of methanol (up to 20%). The fractions containing product were still contaminated with starting material; therefore, a second elution was carried out through silica gel in a 2×3.5 inch Buchner funnel, using chloroform only.

Fractions containing product were pooled and concentrated by rotary evaporation to a solid. Recrystallization from ethanol yielded a white solid which was filtered and dried in vacuo. Yield: 9.38 gm (83%); melting point, 130°–131.5° C.; Rf: 0.89 [chloroform methanol 9:1 (silica)]; Rf: 0.93 [choloroform/acetic acid/methanol 90:5:5 (silica)]. Elemental analysis calculated for $C_{40}H_{44}N_2O_6$ calculated: C, 74.05; H, 6.84; observed: C, 73.90; H, 6.90.

FMOC-(O-t-Butyl)-Tyr-Val

FMOC-(O-t-Butyl)tyr-val-benzyl ester (3.69 gm, 5.70 mMole) was dissolved in 25 ml methylene chloride containing 1 ml acetic acid. To this mixture 1 gm 5% Pd catalyst on activated carbon was added. The system was bubbled with hydrogen for 90 minutes, at which time another 50 mg of catalyst containing 1 ml acetic acid were added. Bubbling was continued for 30 minutes. The catalyst was filtered using Celite and the filtrate concentrated by rotary evaporation to a solid. This solid was dissolved in methanol and precipitated with water. After filtration and vacuum drying, the solid was dissolved in chloroform and precipitated with petroleum ether. Filtration and drying in vacuo yielded pure product; yield: 3.19 gm (100%); melting point, 109°–110° C.; Rf: 0.69 [chloroform/acetic acid/methanol 90:5:5 (silica)], 0.49 Methylene chloride/methanol 9:1 (silica)]. Elemental analysis for $C_{33}H_{38}N_2O_6$; calculated C, 70.95; H, 6.85; observed C, 70.77; H, 6.90.

FMOC-(O-t-Butyl) Tyr-Val Hydroxysuccinimide ester

FMOC-(O-t-Butyl)tyr-val (1.0 gm, 1.8 mMole) and N-hydroxysuccinimide (210 mg, 1.8 mMole) were dissolved in 40 ml THF under nitrogen at 0° C. Dicyclohexylcarbodiimide (DCC) was added as a methylene chloride solution (0.5 M, 3.6 ml, 1.8 mMole) and the reaction mixture was incubated for 2 hours with stirring, then stored overnight at 4° C. TLC showed incomplete reaction, so additional DCC was added (0.45 mMole), and the reaction mixture incubated at room temperature for one day. Dicyclohexylurea (DCU) formed was filtered and the filtrate concentrated to a solid, which was triturated with 4% sodium bicarbonate. The solid was filtered, washed with water dried, then crystallized from chloroform/petroleum ether. A white solid was obtained on filtration and air drying. Yield: 761 mg (65%); Rf: 0.75 [chloroform/methanol 9:1 (silica)]. Elemental analysis for $C_{37}H_{41}N_3O_8 \cdot 0.5$ $H_2O$ calculated: C, 66.85; H, 6.37; observed C, 67.04; H, 6.85.

Leu-(FMOC)Lys

BOC-Leu-N-succinimide (BOC-Leu-OSu) was prepared according to the procedure of Anderson et al. [J. Organic Chem. 86:1839 (1964)]. Yield: 4.89 gm (50%): melting point, 111°–112° C. (lit. 116° C.); Rf: 0.83 [chloroform/acetic acid/methanol 85:5:10 (silica)].

BOC-Leu-OSu (1.64 gm, 5.0 mMole) and epsilon-FMOC-lys (1.84 gm, 5.0 mMole) were dissolved in DMF and incubated with stirring for three days. TLC indicated consumption of the leu component, but unreacted lys component remained. Additional BOC-leu-OSu (0.82 gm, 2.5 mMole) was added. After stirring for one day, all of the lys component had reacted. Solvents were removed by rotary evaporation, leaving an oil which was triturated with dilute HCl (pH 2) and chilled. A solid formed, which was filtered and dried in vacuo.

The crude BOC-leu-(FMOC)lys obtained was dissolved in 25 ml TFA and stirred for 1 hour. TFA was removed by rotary evaporation, leaving an oil which was treated overnight with cold ether. The solid which formed was filtered and air dried. Yield; 1.73 gm (58% overall from Boc-leu-OSu); Rf: 0.78 [n-butanol/acetic acid/water 4:1:1 (silica)]; Rf: 0.28 [chloroform/acetic acid/methanol 85:5:10 (silica)]. Some impurities were evident. This material was then eluted on Amberlite CG-400 (Cl- form) with methanol/water 1:1, effecting a partial removal of contaminants. Solvents were removed by rotary evaporation and lyophilization.

FMOC-(O-t-Butyl) Tyr-Val-Leu((FMOC)Lys

The free base of leu-(FMOC)lys was liberated by treating the crude leu-(FMOC)lys HCl salt (545 mg, 1.0 mMole) with diisopropylethylamine (174 ul, 1.0 mMole) in 60 ml THF for 10 minutes with stirring. The precipitate which formed was filtered, and FMOC-(O-t-Butyl)tyr-val-OSu (604 mg, 0.91 mMole) in THF was added. Over the next 5 days, several additional aliquots of leu-(FMOC)lys (free base) were added as TLC indicated consumption of that component (total additional leu-(FMOC)lys HCL added: 210 mg, 0.4 mMole). Solvent was concentrated by rotary evaporation to 20 ml, then the reaction mixture was poured into cold 10% acetic acid. A white precipitate formed, which was filtered, washed with water, crystallized from isopropanol, and dried in vacuo. Yield: 500 mg (48%); melting point, 218° C. (dec.); Rf: 0.83 [chloroform/acetic acid/methanol 90:5:5 (silica)]. Elemental analysis for $C_{60}H_{71}N_5O_{10} \cdot 0.5$ $H_2O$; calculated; C, 69.88; H, 7.04; observed: C, 69.83; H, 7.21.

FMOC-Tyr-Val-Leu-(FMOC)Lys

FMOC-(O-t-Butyl)Tyr-Val-Leu-(FMOC)Lys (400 mg, 0.39 mMole) was dissolved in 50 ml TFA with 2.2 ml anisole and stirred for 30 minutes. After removal of solvents by rotary evaporation and trituration with ether, a solid was obtained. This was filtered, washed with ether, and dried in vacuo. Yield: 375 mg (99%); melting point, 200° C. (decomp.); Rf: 0.42 [chloroform/acetic acid/methanol 90:5:5 (silica)]. Elemental analysis for $C_{56}H_{63}N_5O_{10}.H_2O$; calculated: C, 68.34; H, 6.65; observed: C, 68.60; H, 6.55.

FMOC-Tyr-Val-Leu-(FMOC)Lys-ADR

FMOC-Tyr-Val-Leu-(FMOC)Lys (96 mg, 0.10 mMole) and N-hydroxysuccinimide (13 mg, 0.11 mMole) were dissolved in 20 ml DMF and cooled to 0° C. under nitrogen. 1-Ethyl-3-(3-dimethylaminopropyl)-carbodiimide (EDCI) (21 mg, 0.11 mMole) was added and the reaction mixture stirred for 2 hours. ADR-HCl (59 mg, 0.10 Mmole) and N-methylmorpholine (12 ul, 0.11 mMole) were then added to the reaction mixture, and stirring was continued for 4 days at room temperature. Solvents were removed by rotary evaporation, leaving a red solid which was rinsed with water, then applied to a 2×10 inch silica gel flash chromatography column. Elution was accomplished with chloroform/methanol 95:5. Product fractions were pooled, evaporated and dried in vacuo. Yield: 55 mg (36%); Rf; 0.33 [chloroform/acetic acid/methanol 90:5:5 (silica)]; Rf: 0.20 chloroform/methanol 95:5 (silica)]. Elemental analysis for $C_{83}H_{90}N_6O_{20}.2.0\ H_2O$; calculated: C, 65.26; H, 6.20; observed: C, 65.37; H, 6.18.

The FMOC moieties were removed from FMOC-Tyr-Val-Leu-(FMOC)Lys-ADR to yield Tyr-Val-Leu-Lys-ADR (14), as described in Section 6.1.1. for FMOC-gly-ADR, except that the exposure time to diethylamine was 1.25 hours (in order to obtain complete reaction, as monitored by HPLC).

7.1.15. VALYL-LEUCYL-LYSYL-VALYL-ADR (15)

FMOC-Val-Leu-t-Butyl Ester

FMOC-val (1.5 g, 4.42 mMole) and N-hydroxysuccinimide (525 mg, 4.56 mMole) were dissolved in $DMF/CH_2Cl_2$ under nitrogen and cooled to −5° C. Dicyclohexylcarbodiimide (DCC) (8.85 ml, 0.5M in methylene chloride, 4.42 mMole) was added and the mixture was stirred at 0° C. for 1 hour, then at room temperature for 1 hour. Precipitate was filtered, and to the filtrate was then added a mixture of leu-t-butyl ester hydrochloride (990 mg, 4.42 mMole) and N-methylmorpholine (0.5 ml, 4.55 mMole) in DMF. Stirring was maintained for 14 days at room temperature, during which time an additional 1.0 equivalent N-methylmorpholine was added. Solvents were then removed by rotary-evaporation, leaving a crude oil which was redissolved in ethyl acetate and extracted sequentially with 10% acetic acid, water, saturated sodium bicarbonate solution, and water. The organic layer was concentrated by rotary evaporation, and further purified by flash Chromatography (2×6 inch silica gel column, petroleum ether/ethyl acetate 9:1). Appropriate fractions were combined and concentrated to dryness. Yield: 713 mg (32%). Elemental analysis for $C_{30}H_{40}N_2O_5$: calculated, C, 70.84; H, 7.93; N, 5.51; observed, C, 70.72; H, 7.98; N, 5.43.

FMOC-Val-Leu

FMOC-val-leu-t-butyl ester (4.00 g, 7.86 mMoles) was dissolved in 15 ml $CH_2Cl_2$ under $N_2$ and treated with 15 ml trifluoroacetic acid and 0.5 ml anisole for 2 hours. Solvents were removed by repeated rotary evaporations from ether suspensions. Crude product was triturated with ether at 0° C., then filtered and dried in vacuo. Yield: 3.04 g (86%). Melting point 156°–159° C. Rf: 0.13 (silica, chloroform/ethyl acetate 3:1). Elemental analysis for $C_{26}H_{32}N_2O_5$, calculated, C, 69.01; H, 7.12; N, 6.19; observed, C, 68.75; H, 7.22; N, 6.10.

FMOC-Val-Leu-(FMOC)Lys

FMOC-val-leu (391 mg, 0.86 mMole) and N-hydroxysuccinimide (108 mg, 0.94 mMole) were dissolved in DMF/CH under nitrogen and cooled to −5° C. Dicyclohexylcarbodiimide (DCC) (1.73 ml, 0.5M in methylene chloride, 0.87 mMole) was added and the mixture was stirred at 0° C. for 1 hour, then at room temperature for 24 hours. Precipitate was filtered, and to the filtrate was then added a suspension of epsilon-FMOC-lys (318 mg, 0.86 mMole) in 15 ml DMF. Stirring was maintained for 7 days. Solvents were then removed by rotary evaporation, leaving a crude product which was purified by flash chromatography (2×7 inch silica gel column, chloroform/methanol/acetic acid step gradient 97:3:0.1 to 95:5:0.1). Appropriate fractions were combined and concentrated to dryness. Yield: 410 mg (60%). Melting point 195°–196° C. Elemental analysis for $C_{47}H_{54}N_4O_8.\ 0.25\ H_2O$: calculated C, 69.91; H, 6.80; N, 6.94. observed C, 69.90; H, 7.01; N, 6.95.

FMOC-Val-Leu-(FMOC)Lys-Val-ADR

FMOC-val-leu-(FMOC)lys (100 mg, 0.11 mMole), N-hydroxybenzotriazole (19 mg, 0.14 mMole), and N-methylmorpholine (15 ul, 0.13 mMole) were dissolved in dry, amine-free DMF at 0° C. After stirring for 10 minutes, Bis(2-oxo-3-oxazolidinyl)-phosphinic acid (BOP-Cl, 33 mg, 0.13 mMole) was added and stirring maintained for 15 minutes. Then a suspension of val-ADR (5) (71 mg, 0.10 mMole) and N-methylmorpholine (25 ul, 0.23 mMole) in DMF was added. Stirring at 0° C. was maintained for 1 hour. An additional increment (0.07 mMole) of activated peptide was prepared by the same procedure and added to the reaction mixture at 0° C. After one hour the mixture was gradually warmed to room temperature and stirred for an additional 15 hours. After rotary evaporation, the crude product was purified by flash chromatography twice (1×6 inch silica gel column, $CHCl_3$/methanol 100:0 to 97:3). Appropriate fractions were combined and rotary evaporated to dryness. Yield 72 mg (55%). Rf: 0.61 (silica, chloroform/methanol 9:1). Elemental analysis for $C_{79}H_{87}N_6O_{19}.2.5.H_2O$: calculated, C, 64.57; H, 6.31; N. 5.72; observed, C, 64.45; H, 6.59; N, 5.75.

Val-Leu-Lys-Val-ADR

The FMOC moiety was removed from FMOC-val-leu-(FMOC)lys-val-ADR to yield val-leu-lys-val-ADR (15) as described for gly-ADR (1). Yield of (15).HOAc was 25 mg (40%). Elemental analysis for $C_{53}H_{69}N_6O_{15}.3.OHOAc.5H_2O$, calculated: C, 54.49; H. 7.05; N, 6.46; observed: C, 54.54; H. 7.08; N. 6.76.

7.1.16. VALYL-LEUCYL-LYSYL-ALANYL-ADR (16)

FMOC-Val-Leu-(FMOC)Lys-Ala-ADR

FMOC-val-leu-(FMOC)lys was coupled to ala-ADR by a similar method to that used for the synthesis of FMOC-val-leu-(FMOC)lys-val-ADR. Quantities of reagents used were: FMOC-val-leu(FMOC)lys (133 mg, 0.15 mMole). N-hydroxybenzotriazole (28 mg, 0.21 mMole), N-methylmorpholine (17 ul, 0.15 mMole), BOP-Cl (38 mg, 0.15 mMole), and as a suspension in DMF: ala-ADR.HOAc (2) (97 mg, 0.14 mMole) and N-methylmorpholine (33 ul, 0.30 mMole). After flash chromatography, 78 mg (39%) of FMOC-val-leu-(FMOC)lys-ala-ADR was obtained. Rf: 0.27 (silica, chloroform/methanol 94:6). This material was deprotected without further characterization.

Val-Leu-Lys-Ala-ADR

The FMOC moeity was removed from FMOC-val-leu-(FMOC)lys-ala-ADR to yield val-leu-lys-ala-ADR (16) as described for gly-ADR (1). Yield of (16).HOAc was 22 mg (38%). Elemental analysis for $C_{47}H_{66}N_6O_{15}.2HOAc.5.5\ H_2O$, calculated: C, 52.16; H, 7.30; N. 7.16; observed: C, 52.09; H, 7.07; N. 7.56.

7 1.17.
GLUTAMYL-(GAMMA-HYDRAZIDE)-ALPHA-ADR (17)

FMOC-Glu-alpha-t-butyl ester

Glutamic acid-alpha-t-butyl ester (5.90 gm, 29.0 mMole was added with stirring to a solution of sodium bicarbonate (2.42 gm, 29.0 mMole) in 120 ml water/acetone (1:1) at room temperature. 9-Fluorenylmethyl succinimidyl carbonate (9.77 gm, 29.0 mMole) was then added to the homogeneous solution and stirring continued for 4 hours. Volatile organics were removed by rotary evaporation. The resulting aqueous suspension was extracted extensively with ether. Combined ether extracts were dried over sodium sulfate, then concentrated by rotary evaporation until turbid. Crystals formed on further cooling. These were filtered and air dried. Yield: 10.6 gm (86.5%); melting point, 106°–108° C.; Rf: 0.84 [chloroform/acetic acid/methanol 90:5:5 (silica)]. $C_{24}H_{27}NO_6$; calculated: C, 67.75; H, 6.40; Observed: C, 67.59; H, 6.45.

FMOC-Glu-alpha-t-butyl-ester-gamma-(N,-FMOC-Hydrazide)

FMOC-glutamic acid-alpha-t-butyl ester (2.00 gm, 4.7 mMole) and 2,4-dinitrophenol (0.95 gm, 5.1 mMole) were dissolved in 50 ml ethyl acetate under a nitrogen atmosphere. After cooling to 0° C., DCC (0.5M, 9.5 ml, 4.75 mMole) was added. The reaction mixture was incubated with stirring at 0° C. for 1 hour. Then the reaction mixture was gradually warmed to room temperature and incubated with stirring for 24 hours. Formation of the active ester was confirmed by TLC [Rf: 0.92 [chloroform/ethyl acetate 3:1 (silica)]; 0.95 [chloroform/methanol 95:5 (silica)]. The DCU precipitate formed was filtered, and the filtrate was added directly to 9-fluorenylmethyl carbazate (1.20 gm, 4.72 mMole). After 24 hours stirring, additional 9-fluorenylmethyl carbazate (0.120 gm, 0.47 mMole) was added. The reaction mixture was incubated with stirring for another 24 hours, and solvents were then removed by rotary evaporation. The resulting oil was dissolved in ethyl acetate and extracted with 5% aqueous sodium carbonate (until no further yellow color appeared in the aqueous layer) and twice with water. The crude product was preadsorbed onto sodium sulfate and then applied to a 1×9 inch silica gel (230–400 mesh) flash chromatography column. Elution was carried out in stages: (1) with petroleum ether/ethyl acetate 2:1; (2) with petroleum ether/ethyl acetate 1:1; and (3) with ethyl acetate. Product eluted with the ethyl acetate wash. Appropriate fractions were combined and evaporated to a solid, then redissolved in ethyl acetate and precipitated with petroleum ether. A solid was filtered and dried in vacuo. Yield: 2.43 gm (80.0%); melting point, 144.5°–147° C.; Rf: 0.26 [chloroform/ethyl acetate 3:1 (silica)]. Elemental analysis for $C_{39}H_{39}N_3O_6$; calculated: C, 70.78; H, 5.94; observed: C, 70.71; H, 5.98.

FMOC-glu-gamma-(N'-FMOC-Hydrazide)

FMOC-glutamic acid-alpha-t-butyl ester-gamma-(N'-FMOC-hydrazide) (2.00 gm, 3.0 mMole) was dissolved in 50 ml TFA plus 2 ml anisole and stirred for 75 minutes at room temperature. Solvents were removed by rotary evaporation leaving an oil, to which ether was added. Traces of TFA were removed by further rotary evaporation to dryness. Ether was added to the solid which was obtained and, after cooling for 2 hours, the solid was filtered, washed with ether, and air dried. Yield: 1.65 gm (91.0%); melting point, 160°–163° C.; Rf: 0.52 [chloroform/acetic acid/methanol 90:5:5 (silica)]. Elemental analysis for $C_{35}H_{31}N_3O_7.0.5\ H_2O$; calculated: C, 68.39; H, 5.24; observed: C, 68.90; H, 5.35.

FMOC-Glu-gamma-(N'-FMOC-Hydrazide)-alpha-3'-ADR

FMOC-glu-gamma-(N'-FMOC-hydrazide) (200 mg, 0.33 mMole) was dissolved in 5 ml freshly nitrogen-bubbled DMF and cooled to 0° C. under nitrogen. N-Methylmorpholine (36 ul, 0.33 mMole) was added and the reaction mixture incubated for 5 minutes. Isobutylchloroformate (42 ul, 0.33 mMole was then added. A suspension of ADR-HCl (230 mg, 0.40 mMole) and N-methylmorpholine (44 ul, 0.40 mMole) in DMF was added dropwise after an activation time of four minutes. The mixture was stirred for 1 hour at 0° C. and then incubated with stirring overnight at 4° C. Solvents were removed by rotary evaporation. The oily residue was dissolved in chloroform/methanol (95:5), applied to a 2×10 inch silica gel (230–400 mesh) flash chromatography column, and eluted with the same solvent system. Appropriate fractions were combined and rotary evaporated to a solid residue. The residue was suspended in ether, filtered, and dried in vacuo over phosphorous pentoxide ($P_2O_5$) at 30° C. Yield: 245 mg (77%); melting point 180°–193° C. (dec.); Rf: 0.35 [chloroform/acetic acid/methanol 90:5:5 (silica)]; Rf: 0.31 [chlororform/methanol 95:5:5 (silica)]. Elemental analysis for $C_{62}H_{58}N_4O_{17}.1\ H_2O$; calculated: C, 64.79; H, 5.26; N, 4.90; observed: C, 64.70; H, 5.45; N, 4.70.

The FMOC moiety was removed from FMOC-glu-(gamma-hydrazide)-alpha-ADR to yield glu-(gamma-hydrazide)-alpha-ADR (17).2 HOAc as described above in Section 7.1.1. Yield of (17) was 16 mg (89%), melting point 188° C. (dec.). Elemental analysis for $C_{36}H_{46}N_4O_{17}.2.0\ H_2O$; calculated: C, 51.29; H, 5.98; N, 6.68; observed: C, 50.89; H, 5.46; N. 6.42.

7 1.18.
GLU-(ALPHA-HYDRAZIDE)-GAMMA-ADR (18)

FMOC-Glu-gamma-t-butyl ester-alpha-(N'-FMOC-Hydrazide)

This compound was prepared by a method identical to that used for the preparation of FMOC-glu-alpha-t-butyl ester-gamma-(N'-FMOC-hydrazide), using commercially available FMOC-glutamic acid-gamma-t-butyl ester as the starting material. Yield: 2.46 gm (79.0%); melting point, 141°–144° C.; Rf: 0.56 [chloroform/ethyl acetate 3:1 (silica)]. Elemental analysis for $C_{35}H_{31}N_3O_7.0.5\ H_2O$; calculated: C, 68.91; H, 5.24; observed: C, 68.71; H, 5.39.

FMOC-Glu-alpha-(N'-FMOC-Hydrazide)

This compound was prepared by a method identical to that used for preparation of FMOC-glutamic acid-gamma-(N'-FMOC-hydrazide) using FMOC-glu-gamma-t-butyl-ester-alpha-(N'-FMOC-hydrazide) as the starting material. Yield, 1.19 gm (66.0%); melting point, 174°–177° C.; Rf, 0.13 [chloroform/ethyl acetate 3:1 (silica)]; Rf: 0.84 [chloroform/acetic acid/methanol 90:5:5 (silica)]. Elemental analysis for $C_{39}H_{39}N_3O_7.0.5$ $H_2O$; calculated: C, 68.39; H, 5.24; observed: C, 68.71; H, 5.39.

FMOC-Glu-alpha-(N'-FMOC-Hydrazide)-gamma-3'-ADR

FMOC-glutamic acid-alpha-(N'-FMOC-hydrazide) (222 mg, 0.361 mMole) was dissolved in 10 ml freshly nitrogen-bubbled DMF and cooled to 0° C. under nitrogen. N-Methylmorpholine (40 ul, 0.36 mMole) was added and the reaction mixture incubated for 5 minutes. Isobutylchloroformate (47 ul, 0.36 mMole) was then added. A suspension of ADR-HCl (188 mg, 0.324 mMole) and N-methylmorpholine (38 ul, 0.35 mMole) in DMF was added after an activation time of 4 minutes. The mixture was stirred for 2 hours at 0° C. The reaction was only approximately 50% complete at this point; therefore, a second activation of the glutamyl component was carried out using the following amounts in the same manner as above: FMOC-glutamic acid-alpha-(N'-FMOC-hydrazide) (100 mg, 0.163 mMole), N-methylmorpholine (18 ul, 0.163 mMole), isobutylchloroformate (21 ul, 0.163 mMole). Two hours later, the reaction was approximately 70% complete and another activation of glutamyl component was carried out using the same amounts as those used in the second activation. After 2 hours, the reaction appeared to be 80% complete and solvents were removed by rotary evaporation. The oily residue was dissolved in chloroform/methanol (95:5), applied to a 1×10 inch silica gel (230–400 mesh) flash chromatography column, and eluted with the same solvent system. Appropriate fractions were combined and rotary evaporated to a solid residue. The residue was suspended in ether, filtered, and dried in vacuo over phosphorous pentoxide at 30° C. Yield: 271 mg (74%); Rf: 0.38 [chloroform/acetic acid/methanol 90:5:5 (silica)]; Rf: 0.27 [chloroform/methanol 95:5 (silica)]. Elemental analysis for $C_{62}H_{58}N_4O_{17}.3 H_2O$; calculated: C, 62.83; H, 5.44; observed: C, 62.91; H, 5.41.

The FMOC moiety of FMOC-glu-alpha-(N'-FMOC-hydrazide)-gamma-ADR was removed as described in Section 6.1.1. to yield glu-(alpha-hydrazide)-gamma-ADR (18).2HOAc. Yield of (18): 55 mg (72%). Elemental analysis for $C_{36}H_{46}N_4O_{17}$; calculated: C, 53.59; H, 5.75; observed: C, 53.47; H, 5.84.

7.1.19. HYDRAZIDE SUCCINYL-ADRIAMYCIN (19)

Adriamycin (58 mg, 0.10 mMole) was suspended in THF/DMF (20 ml/10 ml) and to this was added triethylamine (0.10 mMole) dissolved in THF (0.1M). Succinic anhydride (14 mg, 0.14 mMole) was then added and the mixture incubated using stirring for a total of 65 hours. The course of the reaction was followed by TLC (Rf: succinyl-adriamycin product: 0.78; adriamycin: 0.46 [n-Butanol/acetic acid/water 4:1:1 (silica)] until all adriamycin was consumed.

Succinyl-adriamycin (30 mg, 0.05 mMole) was coupled to anhydrous hydrazine as follows: succinyl-ADR was dissolved in dry nitrogen bubbled DMF under nitrogen atmosphere and cooled to 0° C. N-methylmorpholine (1.0 equivalent) was added and the mixture incubated for about 5 minutes. Isobutylchloroformate (1.0 equivalent) was added and the mixture incubated for 3–5 minutes. Anhydrous hydrazine (1.0 equivalent) was added in DMF. The reaction mixture was incubated for 1–2 hours at 0° C., then for 12–16 hours at 4° C. Solvents were removed by rotary evaporation at 35° C. Purification was accomplished by elution on a preparative C-18 reverse phase flash chromatography column, first with water to remove unreacted hydrazine, then with methanol to remove product. Removal of solvents by rotary evaporation and lyophilization gave a red solid. Yield: 31 mg (94%); melting point 165° C. (dec.); Rf: 0.85 [n-butanol/acetic acid/water 4:1:1 (silica)]; Rf: 0.71 [acetonitrile/0.1% TFA 1:1 (reverse phase)].

7.1.20. HYDRAZINOACETYL-ADR (20)

Bis(FMOC)-Hydrazinoacetic Acid

Ethyl hydrazino-acetate HCl (5 gm, 32 mMole) and NaOH (2.8 gm, 71 mMole) were dissolved in 200 ml ethanol/water (1:1) and incubated with stirring for approximately 2 hours at room temperature. The pH was adjusted with concentrated HCl to pH 7.0 and the solvents removed by rotary evaporation to an oil. A TLC-homogeneous product, hydrazino-acetic acid, was obtained. Rf: 0.15 [n-Butanol/acetic acid/water 4:1:1 (silica)].

Hydrazino-acetic acid (4.1 gm, 32 mMole) and sodium bicarbonate (9.4 gm, 112 mMole) were dissolved in THF/water (1:1) at 0° C. 9-Fluorenylmethyl-chloroformate (20.7 gm, 80 mMole) in THF was added dropwise over a 30–60 minute period. The reaction mixture was allowed to warm to room temperature gradually and incubated with stirring at that temperature for 15 hours. The reaction mixture was rotary evaporated to remove volatile components, then extracted with ether to remove FMOC-Cl. The aqueous layer was adjusted to pH 3 with 6M HCl. This precipitated a white solid, which was filtered, washed with petroleum ether, and dried over $P_2O_5$ at 40° C. Yield: 15 gm (88%); melting point, 108°–109° C. (dec.); Rf: 0.73 [chloroform/acetic acid/methanol 90:5:5 (silica)]. Elemental analysis for $C_{32}H_{26}N_2O_6.1.5 H_2O$; calculated: C, 68.43; H, 5.22; N, 5.01; observed: C, 68.71; H, 5.17; N, 5.77.

Bis (FMOC)-hydrazinoacetic acid was coupled to ADR as described in Section 6.1.1. thus forming bis(-FMOC)-hydrazinoacetyl-ADR. Yield of bis (FMOC)-hydrazinacetyl-ADR was 89%; melting point 159° C. (dec.); Rf: 0.58 [chloroform/acetic acid/methanol 90:5:5 (silica)]. Elemental analysis for $C_{59}H_{53}N_3O_{16}$; calculated: C, 66.84; H, 5.04; N, 3.98; observed: C, 66.94; H, 5.53; N, 3.89.

The FMOC moiety was removed as described above to yield hydrazinoacetyl-ADR (20). Yield of deprotected final product: 13 mg (75%). Melting point 206° C. (dec.); Rf: 0.13 [chloroform/acetic acid/methanol 90:5:5 (silica)]; Rf: 0.80 [n-butanol/acetic acid/water 4:1:1 (silica)].

7.1.21. AMINOXYACETYL-ADR (21)

FMOC-Aminoxyacetic Acid

Carboxymethoxylamine hemihydrochloride (106 mg, 0.485 mMole) and N-methylmorpholine (53 ul, 0.485 mMole) were dissolved in 200 ml chloroform/methanol (1:1) under nitrogen at 0° C. A solution of 9-fluorenylmethyl succinimidyl carbonate (325 mg, 0.97 mMole) in chloroform was added dropwise over a 30 minute period. The reaction mixture was warmed to room temperature and incubated with stirring for 15–20 hours. The reaction mixture was then heated to 55° C. and incubated for 3 hours. Solvents were removed by rotary evaporation, and the solid residue was dissolved in ethyl acetate and extracted with 0.1M HCl (5X) and water (4X). The organic layer was dried over sodium sulfate and rotary evaporated to a solid residue, which was washed with ether and dried in vacuo over $P_2O_5$ at 40° C. Yield: 274 mg (90%); melting point, 190° C. (dec.); Rf: 0.58 [chloroform/acetic acid/methanol 90:5:5 (silica)].

FMOC-aminoxyacetic acid was coupled to ADR as described in Section 6.1.1., thus forming FMOC-aminoxyacetyl-ADR. Yield of 42%; melting point 168°–170.5° C.; Rf: 0.38 [chloroform/acetic acid/methanol 90:5:5 (silica)]. Elemental analysis for $C_{44}H_{42}N_2O_{15}.1\ H_2O$; calculated: C, 61.68; H, 5.18; N, 3.28; observed: C, 61.92; H, 5.56; N, 3 11.

The FMOC moiety was removed as described above to yield aminoxyacetyl-ADR (21).HOAc. Yield was 6 mg (25%); melting point 192° C. (dec.); Rf: 0.12 [chloroform/acetic acid/methanol 90:5:5 (silica]; Rf: 0.82 [n-butanol/acetic acid/water 4:1:1 (silica)]. Elemental analysis for $C_{31}H_{36}N_2O_{15}.0.5\ H_2O$; calculated: C, 54.30; H, 5.50; N, 4.10; observed: C, 54.07; H. 5.65; N, 4.77.

7.1.22. HYDRAZINOBENZOYL-ADR (22)

Bis(FMOC)-Hydrazinobenzoic Acid

Hydrazino-benzoic acid (50 mg, 0.33 mMole) and sodium bicarbonate 983 mg, 0.99 mMole) were dissolved in THF/water (1:1) at 0° C. 9-fluorenylmethylchloroformate (213 mg, 0.83 mMole) was added in THF dropwise over a 30–60 minute period. The reaction mixture was allowed to warm gradually to room temperature and incubated with stirring at that temperature for 15 hours. The reaction mixture was rotary evaporated to remove volatile components, then extracted with ether to remove 9-fluorenylmethylchloroformate. The aqueous layer was adjusted to pH 3 with 6M HCl. This precipitated a white solid, which was filtered, washed with petroleum ether, and dried over $P_2O_5$ at 40° C. Yield: 114 mg (58%):, melting point, 146°–148° C. (dec.); Rf: 0.71 [ethyl acetate/petroleum ether 1:1 (silica)]. Elemental analysis for $C_{37}H_{28}N_2O_6$; calculated: C, 74.47; H, 4.73; N, 4.72; observed: C, 74.60; H, 4.77; N. 4.66.

Bis(FMOC)-hydrazinobenzoic acid was coupled to ADR as described in Section 7.1.1. Yield of bis (FMOC)-hydrazinobenzoyl-ADR was 86%; melting point 174°–176° C.; Rf: 0.65 [chloroform/acetic acid/methanol 90:5:5 (silica)]. Elemental analysis for $C_{64}H_{55}N_3O_{16}.1\ H_2O$; calculated: C, 67.42; H, 5.04; N, 3.70; observed: C, 67.65; H, 5.63; N, 3.68.

The FMOC moiety was removed as describe above to yield hydrazinobenzoyl-ADR (22).2HOAc, with the exception that the exposure time to diethylamie was 1.5 hours. There was a slight amount of aglycone formation observed, however, extraction as described above was successful in removing the aglycone formed. Yield of (22): 13 mg (36%).

7.1.23. HYDRAZINOACETYL-TYR-ALA-ALA-ALA-ADR (23)

Bis(FMOC)-hydrazinoacetic acid prepared as described in Section 7.1.12 was coupled to tyr-ala-ala-ala-ADR (13) as described above for gly-ADR in Section 7.1.1. Yield of 58%; melting point 188° C. (dec.); Rf: 0.10 [chloroform/acetic acid/methanol 90:5:5 (silica)]; Rf: 0.86 [n-butanol/acetic/acid water 4:1:1 (silica)]. Elemental analysis for $C_{77}H_{77}N_7O_{21}.2.5\ H_2O$; calculated: C, 63.14; H, 4.47; N, 6.72; observed: C, 63.26; H, 5.89; N, 6.46.

The FMOC moiety was removed as describe above yielding hydrazinoacetyl-tyr-ala-ala-ala-ADR (23).2HOAc. Yield of 15 was 12 mg (80%), melting point 200° C. (dec); Rf: 0.50 [n-butanol/acetic acid/water 3:1:1 (silica)]; Rf: 0.44 [methylene chloride/methanol/water 100:20:1 (silica)].

7.2. ADR AND DNR 13-HYDRAZONE DERIVATIVES

C-13-hydrazones of ADR and DNR have been synthesized by condensation of an acid hydrazide with the C-13 ketone moiety of ADR or DNR.

7.2.1 ADRIAMYCIN-ADIPIC DIHYDRAZIDE (24)

Adriamycin-adipic dihydrazide (ADR-ADH) was synthesized as follows:

ADR-HCl (145 mg, 0.25 mMole) and adipic dihydrazide (4.35 gm, 25 mMole) were dissolved in a mixture of water/methanol (75 ml/25 ml). The mixture was protected from light and allowed to stand for 13 days at room temperature. The course of the reaction was followed by TLC (Rf, product: 0.29, adriamycin: 0.48 [acetonitrile/0.5% acetic acid 1:1 (reverse phase plate)] and by HPLC (C-18 reverse-phase; isocratic methanol/3% ammonium carbonate 65:35). When the reaction was at equilibrium as judged by HPLC (<10% adriamycin), solvents were removed by rotary evaporation and lyophilization. The residue was redissolved in water and applied to a 1×15 inch C-18 bonded silica column which had been equilibrated with water. The column was washed with 2 liters water to remove unreacted adipic dihydrazide. Crude product was then eluted by washing with methanol. Solvents were removed by rotary evaporation and a final lyophilization. A fluffy red solid was obtained (130 mg, 70% yield) which was free of unreacted adipic dihydrazide but which did contain adriamycin (<5%) by HPLC analysis. Yield: 130 mg (70%).

7.2.2. ADR-PENTAGLUTAMYLHYDRAZIDE (25)

ADR-pentaglutamylhydrazide was synthesized as follows:

BOC-(Glutamyl-gamma-benzyl ester)4-Resin

Starting from BOC-glutamic acid-(gamma-benzyl ester)-Merrifield resin (20.0 gm, 0.43 mEquiv/gm, 8.6 mMole), each subsequent glutamyl residue was added by three sequential reactions with the symmetrical anhydride of BOC-glutamic acid-(gamma-benzyl ester) using standard peptide solid phase synthesis techniques. The symmetrical anhydride was synthesized as follows: Boc-glutamic acid-gamma-benzyl ester (8.7 gm, 26 mMoles) was dissolved in methylene chloride at 0° C. under nitrogen. To this was added DCC (2.7 gm, 13 mMoles) and the solution was stirred for 2 hours. After filtration of the DCU precipitate and drying over magnesium sulfate, the solution was concentrated to an oil by rotary evaporation, dissolved in DMF, and added to the deprotected resin.

Phthaloyl-(Glutamyl-gamma-ethyl ester)-(Glutamylgamma-benzyl ester)$_4$-Resin

The symmetrical anhydride of phthaloyl-glutamic acid-(gamma-ethyl ester) (4.6 mMole) was formed as above and added to deprotected tetraglutamyl-resin (8.55 gm, 2.87 mMole).

Pentaglutamyl-hexahydrazide

Pentaglutamyl resin (4.34 gm, 1.44 mMole), formed in the previous step, was suspended in 22 ml DMF with 9.6 ml anhydrous hydrazine and stirred at room temperature for two days. The resin was then filtered and washed sequentially with DMF, methanol, methylene chloride, methanol, methylene chloride, and DMF. The washings were combined and rotary evaporated to an oil. Treatment with methanol formed a solid, which was filtered and dried in vacuo, yielding crude peptide-hydrazide. Yield: 1.50 gm (100%); melting point, 200° C. (dec.); positive Ehrlich's test for hydrazide.

ADR-Pentaglutamylhydrazide

Pentaglutamyl-hexahydrazide (28.6 mg, 0.038 mMole) and ADR-HCl (110 mg, 0.19 mMole) were suspended in 10 ml water, protected from light, and stirred gently for two days. The reaction mixture was allowed to stand for an additional four weeks. Partial purification was accomplished by passage through a Sephadex LH-20 column, eluting with water, and pooling of appropriate fractions. Lyophilization of the pooled fractions yielded the pentaglutamylhydrazide-ADR product.

7.2.3. DAUNORUBICIN-ADH (26)

This synthesis was identical to that of (24), with the exception that a shorter reaction time (4 days) was sufficient for complete reaction.

7.2.4. IDARUBICIN-ADH HYDRAZONE (27)

This synthesis was identical to that of ADR-ADH (24), with the exception of that a shorter reaction time (1 day) was sufficient for complete reaction. Yield of (27) was 54%.

7.2.5. [$^3$H]-DIMETHYLADRIAMYCIN-ADH (28)

Two steps were involved in the synthesis of Dimethyladriamycin-ADH (Me$_2$ADR-ADH). The first step involves the methylation at the amino group located in the amino-sugar side chain. The C-13 hydrazone derivative of Me$_2$ADR is prepared in the second step.

[$^3$H]-3'-N,N-Dimethyladriamycin

A solution of ADR HCl (48 mg, 0.083 mMole) in 2-ml CH$_3$CN/H$_2$O (1:1) was stirred in the dark with a solution of [$^3$H]-CH$_2$O (50 mCi, 60 mCi/mMole, 0.833 mMole, 2.5 ml) in H$_2$O, and this mixture was immediately added dropwise to a solution of NaBH$_3$CN (11 mg, 0.167 mMole) in 1 ml CH$_3$CN. The addition period was 10 minutes. Stirring was then continued for an additional 20 minutes. The reaction was extracted with CH$_2$Cl$_2$ (4×1 ml). The pooled organic extracts were evaporated to a film using a N$_2$ stream. The film was redissolved in 2 ml MeOH and applied among four preparative TLC plates (Analtech Uniplate, taper plate, silica gel GF). The appropriate band [Rf 0.31-0.38, CHCl$_3$/MeOH/H$_2$O (40:10:1)] was scraped from each of the plates, pooled, and washed with CHCl$_3$/MeOH (8:2). The washings were treated with 4 drops glacial HOAc and evaporated to a film with a N$_2$ stream. TLC (Analtech silica gel GHLF, CHCl$_3$/MeOH/H$_2$O [40:10:1], Rf. 0.34) and HPLC (Rainin Microsorb C-18; MeOH/H$_2$O 65:35 with 3% NH$_4$OAc) analyses indicated a homogeneous product. Yield: 7 mg (13.5%).

[$^3$H]-3'-N,N-Dimethyladriamycin-Adipic Dihydrazide Hydrazone

The film residue from step 1 was dissolved in 1 ml MeOH along with 3 drops glacial HOAc, then stirred with a suspension of adipic dihyrazide (195 mg, 1.12 mMole) in 2 ml H$_2$O until all had dissolved. The reaction was allowed to stand in the dark for 9 days, at which time solvents were removed using a N$_2$ stream. The residue was redissolved in 1 ml H$_2$O and applied to a small C-18 reverse phase HPLC column. After washing with approximately 500 ml H$_2$O partially purified product was eluted with methanol. Solvents were evaporated with N$_2$. HPLC analysis of this material showed it to be of similar composition to previous preparations of ADR-ADH; it contains 5-10% unreacted parent anthracycline and ADH-anthracycline dimer. The overall isolated yield in this second step was 5 mg (56%), and the product contained 367 uCi at a specific activity of 58.3 mCi/mMole.

7.3. 14-THIOETHER DNR DERIVATIVE

7.3.1. DNR-14-S-(3-PROPIONYL HYDRAZIDE)(290)

14-Bromo-DNR (50 mg) was mixed with K$_2$CO$_3$ (12 mg) in 10 ml dry methanol under nitrogen at 0° C. 2-Mercaptopropionyl hydrazide (14 mg) dissolved in 5 ml methanol was added and the reaction mixture incubated with stirring for 40 minutes at 0° C. Solvents were stripped using a stream of nitrogen, leaving an impure solid which was shown on TLC to be a mixture of 2 components presumed to be the S-alkylation and N-alkylation products.

To avoid the undesirable N-substitution, N-FMOC-3-mercapto-propionyl hydrazide could be synthesized. This should yield only the thio-ether after deprotection.

8. PREPARATION OF ANTIBODY CONJUGATES

8.1. ADR-ADH-ANTIBODY CONJUGATE

In one series of experiments, ADR-ADH-antibody conjugates were prepared according to the present invention as follows:

A murine monoclonal antibody, designated B72.3, specific for an antigen of human adenocarcinoma (Colcher et al., 1981, Proc. Nat'l Acad. Sci. USA 78:3199-03) obtained from Celltech was used.

The oligosaccharide moiety of the B72.3 antibody was oxidized by incubation, in the dark, with 10 mM NaIO$_4$ in phosphate buffered saline (PBS; 0.15M NaCl, 0.01M PO$_4^{-2}$, pH 6.0) for 1 hour on ice. Excess NaIO$_4$ was removed from the oxidized antibody by dialysis against PBS. The modified antibody (1.2 mg/ml) in PBS was then incubated with ADR-ADH at 30 fold excess for 3 hours at 37° C. Unreacted ADR-ADH was removed by elution of the reaction mixture through Dowex 50W column with PBS, pH 7.5. The ADR-ADH-B72.3 conjugates recovered were analyzed by gel filtration HPLC on a Biosil TSK 250 column with a cationic detergent mobil phase, cetyltrimethyl ammonium bromide (0.5% CTAB, 0.05M NaOAc, 0.1M NaCl). No free ADR-ADH was detectable following elution through the Dowex 50w column (2 ml resin/100 mg conjugate, pH 7.0). The final antibody concentration of the conjugate was 2.4 mg/ml and the conjugate contained 1.6 mole ADR-ADH per mole B72.3.

8.2. [$^3$H-Me$_2$ADR-ADH-ANTIBODY CONJUGATE

[$^3$H]-Me$_2$ ADR-ADH was coupled to an oxidized moiety of B7.23 to form a highly aqueous soluble conjugate with a specific activity of 77,000 cpm/500 ug and containing 3.5 moles [$^3$H]-Me$_2$ADR/mole antibody.

8.3. IDARUBICIN-ADH-ANTIBODY CONJUGATE

Idarubicin-ADH was coupled to an oxidized moiety of B72.3 to form a highly aqueous soluble conjugate containing 3.8 moles IDA/mole antibody.

8.4. ADR-PENTAGLUTAMYL HYDRAZIDE ANTIBODY CONJUGATE

ADR-pentaglutamyl hydrazide was coupled to an oxidized carbohydrate moiety of R9.75 to form a highly aqueous soluble conjugate containing 6 moles ADR-/mole antibody.

8.5. ADR-GLU-(GAMMA-HYDRAZIDE) (ADR-E-GAMMA-Hy)-ANTIBODY CONJUGATE

ADR-E-gamma Hy was coupled selectively to the oxidized carbohydrate moiety of B72.3 or S4 antibody by incubation at 20 fold excess in 0.05M MOPS, MES or bicarbonate buffer to form ADR-Glu-gamma-Hydrazide-Antibody conjugate (2.5 moles ADR/mole antibody).

8.6. ADR-GLU-(ALPHA-HYDRAZIDE)(ADR-E-ALPHA-Hy)-ANTIBODY CONJUGATE

ADR-E-alpha-Hy was coupled selectively to the oxidized carbohydrate moiety of B72.3 or S4 antibody by incubation at 20 folds excess in MOPS (pH 6.0) to form ADR-Glu-alpha-Hydrazide antibody conjugate with slight aggregate formation (2 mole ADR/mole antibody).

9. THERAPEUTIC EFFECTS OF SITE SELECTIVE ADRIAMYCIN-ADIPIC DIHYDRAZIDE-ANTIBODY CONJUGATE

9.1. THERAPEUTIC EFFECTS AGAINST HUMAN ADENOCARCINOMA OF THE COLON

The following series of experiments demonstrate that a site selective adriamycin-adipic acid dihydrazide (ADR-ADH) and adriamycin-alpha glutamyl-gamma hydrazide (ADR-E-gamma Hy) anti-tumor antibody conjugates prepared according to the present invention, exert significant therapeutic effects against adenocarcinoma tumor xenografts when administered in vivo. In contrast, ADR-ADH alone or site selectively attached to irrelevant antibody results in no difference in tumor xenograft growth when compared to untreated animals.

The tumor cell line used in these experiments was a human colon adenocarcinoma tumor BL/CX-3 obtained from Bogden Laboratories (Worchester, Mass.). This cell line was established in nude mice from a fresh surgical explant of a metastasis obtained from a 50 year old male at St. Joseph's Hospital (Houston, Tex.). Preliminary experiments (results not shown) indicated that the BL/CX-3 cell line is sensitive to ADR (sub-renal capsule assay) and expresses the TAG-72 antigen specifically recognized by monoclonal antibody B72.3 described by Colcher et al. (1982, Proc. Nat'l Acad. Sci. USA 78:3199-03).

In one experiment, a tumor-specific ADR-ADH-antibody conjugate was prepared using B72.3 antibody (obtained from Celltech) as described in Section 8 (referred to as "ADR-ADH-B72.3"). An irrelevant ADR-ADH-antibody conjugate was also prepared using R9.75 antibody, specific for class I Major Histocompatability antigen of Brown Norway rats (see Smilek et al., 1980, J. Exp. Med. 151:1139) as described in Section 8.

The in vivo therapeutic effects were evaluated in femal nude mice (NIH Swiss Webster, Taconic Farms, Germantown, N.Y.) weighing an average of 28 gms injected subcutaneously on day 0 with about a 3 mm cube of BL/CX3 at the fourth serial mouse passage.

Eighty tumor-bearing mice were divided into 8 groups of 10 mice each. Beginning on day 7 when tumors became measurable, animals were injected intravenously (via tail vein) with therapeutic agents on days 7, 14, 21, 28 and 35 according to the following treatment protocol:

Group 1 (control), no treatment;
Group 2, 0.92 mg purified B72.3 antibody (tumor specific antibody);
Group 3, 1.0 mg purified R9.75 antibody (irrelevant antibody);
Group 4, 6 ug ADR-ADH-B72.3 (0.96 mg) (tumor specific ADR-ADH conjugate);
Group 5, 10 ug ADR-ADH-R9.75 (0.99 mg) (irrelevant ADR-ADH conjugate);
Group 6, 200 ug ADR-ADH;
Group 7, 200 ug ADR [about 7 mg/kg body weight; maximum tolerated dose (mtd) per animal]; and
Group 8, 200 ug ADR plus 0.92 mg B72.3 (specific antibody+drug mixture).

Animals were weighed and tumors measured (length and width) every 2 or 3 days from day 7 to day 76. Results are graphically illustrated in FIG. 1 (A-F).

As demonstrated in FIG. 1 (A-F), tumor growth in animals treated with the site selective ADR-ADH-(B72.3) conjugate (Group 4, FIG. 1C) was significantly inhibited compared to the untreated group (P 0.05 on days 12–40). The tumor inhibitory effect appears equivalent to that seen in animals receiving 200 ug ADR alone, i.e., about the maximally tolerated dose of ADR, for about 35 days. The inhibition of tumor growth lasts beyond day 35, the end of treatment.

As demonstrated in the FIG., by day 21 following injection of tumor xenografts, statistically significant inhibition of tumor growth was observed in those animals treated with site selective ADR-ADH-(B72.3) conjugate (Group 4) compared to to untreated animals (Group 1). In contrast, animals treated with ADR-ADH irrelevant antibody conjugate (Group 5) showed no difference from the untreated group.

Statistically significant inhibition of tumor growth was also seen in those animals treated with ADR at the maximally tolerated dose either alone (Group 7) or in mixture with antibody specific for the tumor (Group 8).

On the other hand, the tumor growth observed in animals which were treated with ADR-ADH at an equivalent dose (Group 6, 200 ug) was not significantly different from that observed in untreated animals.

In another experiment, tumor-specific ADR-ADH-B72.3 antibody conjugate was prepared as above. Tumor specific ADR-E-gamma-Hy-B72.3 antibody conjugate was also prepared as described above. An irrelevant ADR-ADH-antibody conjugate and an irrelevant ADR-E-gamma-Hy antibody conjugate were also prepared using S4 antibody, a murine antibody specific for renal cell carcinoma (obtained from Lloyd Old, Memorial Sloan-Kettering, N.Y.) as described above.

One hundred and ten female nude mice (nu/nu Swiss, Taconic Farms Germantown, N.Y.), were divided into 11 groups of 10 animals each. Average weight of the mice was 23.6 gm. On day 0, animals in all groups except Group 1 were injected with about a 3 mm cube of BL/CX3 at the fourth serial passage. Beginning on day 7 when tumors were measurable, animals were injected intravenously (via tail vein) with therapeutic agents on days 7, 14, 21, 20 and 35 as follows:

Group 1, (growth control) non-tumor bearing; no treatment;
Group 2, (control), no treatment;
Group 3, 1.0 mg purified, B72.3 antibody (tumor specific antibody);
Group 4, 190 ug ADR (about mtd per animal)
Group 5, 12.4 ug ADR;
Group 6, 190 ug ADR plus 1.0 mg B72.3 [specific antibody+drug (mtd) mixture];
Group 7, 12.4 ug ADR plus 1.0 mg B72.3 [specific antibody+drug (low dose) mixture];
Group 8, 12.4 ug ADR-ADH-B72.3 (1.06 mg) (tumor specific ADR-ADH conjugate);
Group 9, 12.6 ug ADR-E gamma Hy-B72.3 (1.03 mg) (tumor specific ADR-E-gamma-Hy conjugate)
Group 10, 11.5 ug ADR-ADH-S4 (0.46 mg) (irrelevant ADR-ADH conjugate);
Group 11, about 10 ug ADR-E-gamma-Hy-S4 (0.25 mg) irrelevant ADR-E-gamma-Hy conjugate.

Tumors were measured at 2-4 day intervals from day 7-40. Results are graphically illustrated in FIG. 2 (A-H).

Figure 2H:
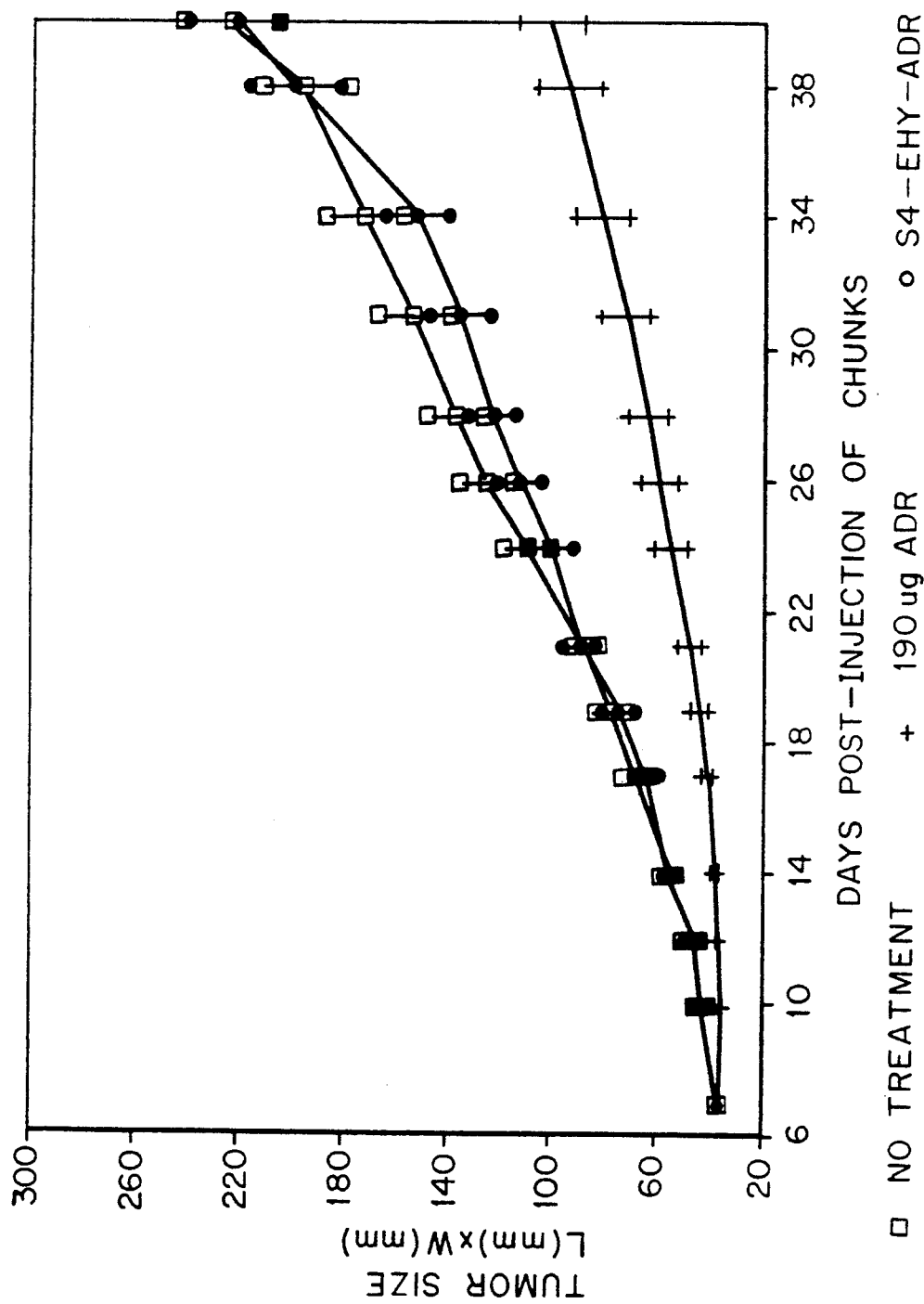

As demonstrated in FIG. 2 (E and F), statisticaly significant inhibition of tumor growth was observed in animals treated with the site selective ADR-ADH-B72.3 conjugate from day 10-24 (Group 8, FIG. 2 E) and in animals treated with site selective ADR-E-gamma-Hy-B72.3 conjugate from day 10-17 (Group 9, FIG. 2 F) compared to results observed on untreated animals (Group 2, FIG. 2 A-H). Thus these confirm and extend those obtained in the experiment described alone. In contrast, animals treated with irrelevant antibody conjugate antibody (Group 10, FIG. 2G and Group 11, FIG. 2H) showed no difference from the untreated group.

Animals treated with drug alone, ADR at the maximally tolerated dose (Group 4 FIG. 2 A-H) showed significant inhibition of tumor growth from day 10-40 which compared to untreated animals. Similarly, tumor growth was inhibited in animals treated with a mixture of tumor specific antibody and ADR at the maximally tolerated dose (Group 6, FIG. 2C). No greater inhibition was observed using the mixture when compared to drug alone at the same dose. Importantly, no significant inhibition, however, was observed in animals treated with a dose of ADR equivalent to that coupled to antibody in the conjugates either alone (Group 5, FIG. 2B) or in a mixture with tumor specific antibody (Group 7, FIG. 2D).

9.2. THERAPEUTIC EFFECTS AGAINST LYMPHOMA XENOGRAFTS

This experiment demonstrates that a site selective ADR-ADH anti-tumor antibody conjugate exerts therapeutic tumor growth inhibitory effects against lymphoma xenografts when administered in vivo.

A tumor-specific ADR-ADH-antibody conjugate was prepared as described above using R9.75 antibody specific for a Brown Norway (BN) rat lymphoma cell line (referred to as "ADR-ADH-R9.75"). An irrelevant ADR-ADH-antibody conjugate was also prepared as described above.

Seventy female nude mice (nu/nu Swiss; Taconic Farms, Germantown, N.Y.) weighing 20-24 gm were divided into 7 groups of 10 mice each. On day 0, all mice except those in Group 1 (non-treated, growth control group) were injected with $1 \times 10^6$ Brown Norway (BN) lymphoma cells. On days 1, 5, 9, 13 and 17, all experimental groups of mice received intravenous injections (via tail vein) of therapeutic agents as follows:

Group 2, tumor-bearing, no treatment;
Group 3, 1.0 mg purified R9.75 antibody (tumor specific antibody alone);
Group 4, 14.3 ug ADR-ADH;
Group 5, 14.3 ug ADR-ADH+1.0 mg R9.75 antibody (mixture);
Group 6, ADR-ADH-R9.75 conjugate (11.2 ug ADR-ADH coupled to 1.0 mg R9.75; 2.3 moles ADR/antibody) (specific conjugate);
Group 7, ADR-ADH-irrelevant antibody conjugate (5.8 ug ADR-ADH coupled to 1.0 mg antibody) (irrelevant conjugate). Animals were weighed and tumors measured (length and width) every other day throughout the study. Results (mean±SEM) are presented graphically in FIG. 3(A-B).

Figure 3B:
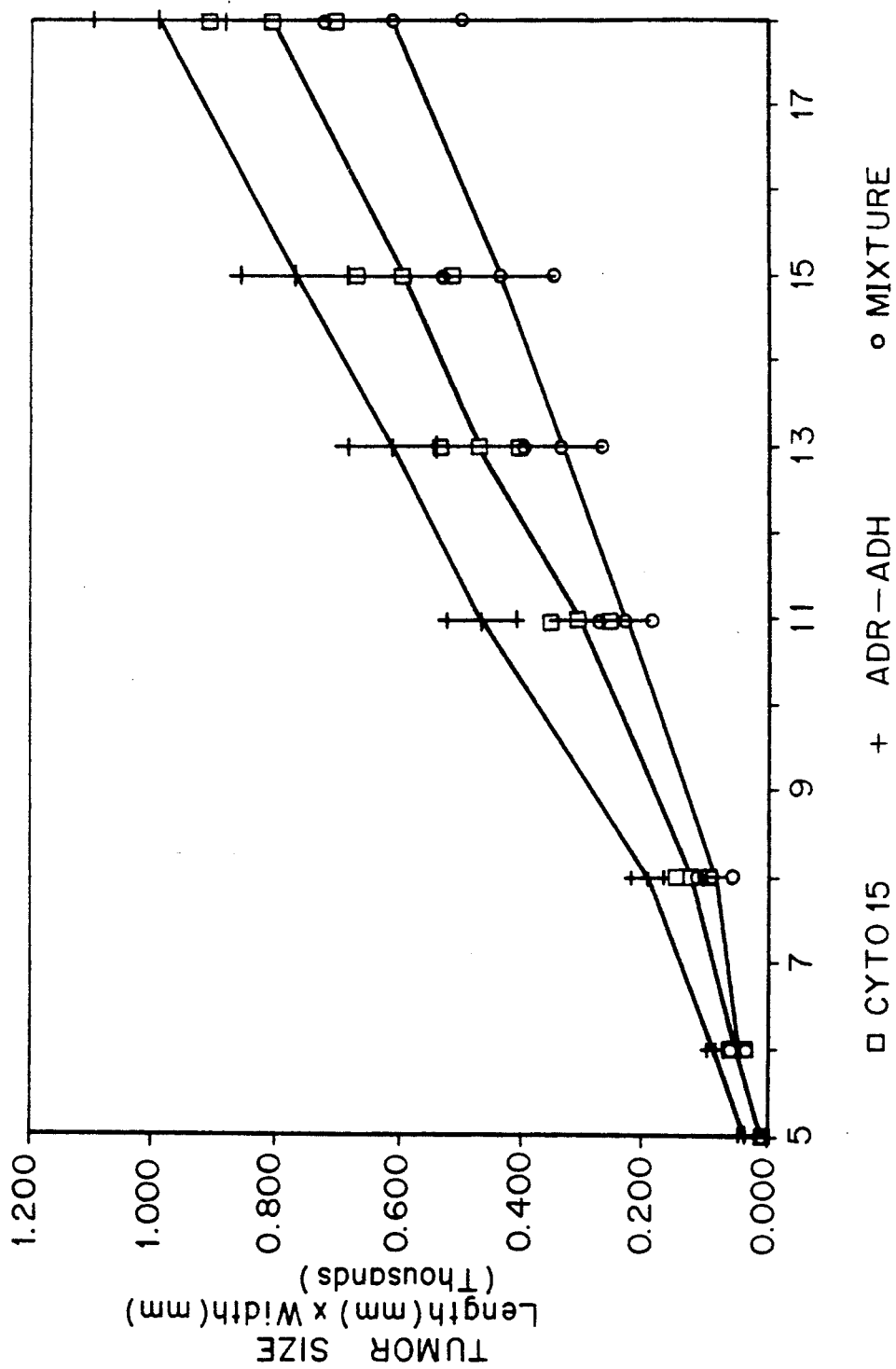

Average tumor growth in animals in untreated controls (Group 2) and in animals receiving the tumor specific ADR-ADH antibody conjugate (Group 6) and irrelevant ADR-ADH antibody conjugate (Group 7) are shown in FIG. 3(A). Average tumor growth in animals receiving ADR-ADH alone (Group 4), a mixture of tumor specific antibody and ADR-ADH (Group 5) and tumor specific antibody alone (Group 3) are shown in FIG. 3(B).

As demonstrated in FIG. 3(A), growth of tumors in animals treated with site selective tumor-specific ADR-ADH conjugate (Group 6) was highly significantly inhibited (p=0.001) compared to untreated tumor-bearing animals (Group 2). In contrast, growth of tumors in animals treated with antibody alone (Group 3) ADR-ADH (Group 4) or ADR-ADH irrelevant antibody conjugate (Group 7) was not significantly different from untreated animals (FIGS. 3A-B). Tumor growth in those animals which received a mixture of ADR-ADH and tumor specific antibody (Group 5) tumor growth was also significantly inhibited as compared to untreated animals (p=0.01).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

10. BIODISTRIBUTION OF B72.3-[³H]-Me₂ADR-ADH

This experiment demonstrates that the ([³H]-dimethyladriamycin-ADH) [³H]-Me₂ADR-ADH antibody conjugate is site specific, i.e. most of the counts are primarily distributed in the tumors of mice administered with adenocarcinoma tumor xenografts.

Radiolabelled Me₂ADR-ADR was prepared by the method described in section 7.2.5. It was then conjugated to the antibody B72.3 using procedures described in section 8.2.

Nude mice weighing on average 25 g were implanted with the human colon adenocarcinoma cell line, LS174T. When the tumors were 10mm × 10mm, usually seven days after implantation, the xenografted and normal (non-tumor bearing) mice were injected and dissected as follows:

| Group | Xenograft | Sample | Dissection |
|---|---|---|---|
| 1 | LS174T | B72.3-[³H]—Me₂ ADR-ADH | Day 3 |
| 2 | LS174T | [³H]—Me₂ ADR-ADH | Day 3 |
| 3 | none | B72.3-[³H]—Me₂ ADR-ADH | Day 3 |
| 4 | none | [³H]—Me₂ ADR-ADH | Day 3 |

The animals were dissected at day 3, organs solubilized using a tissue solubilizer, scintillation fluid added, and then counted in a beta counter. The percent injected dose per gram was calculated. Results are summarized in Table II below and FIG. 4.

TABLE II

| | PERCENT INJECTED DOSE PER GRAM* | | | |
|---|---|---|---|---|
| | LS174T XENOGRAFT | | NON-TUMOR BEARING | |
| ORGAN | B72.3-ADR-ADH | ADR-ADH | B72.3-ADR-ADH | ADR-ADH |
| BLOOD | 0.26(0.10) | 0.21(0.06) | 0.35(0.04) | 0.15(0.03) |
| LUNG | 0.95(0.08) | 0.75(0.20) | 0.76(0.28) | 0.58(0.25) |
| SPLEEN | 1.35(0.23) | 2.30(0.33) | 1.11(0.42) | 1.38(0.76) |
| LIVER | 0.65(0.07) | 0.66(0.17) | 0.69(0.34) | 0.36(0.19) |
| KID-R | 0.35(0.09) | 0.37(0.07) | 0.49(0.34) | 0.34(0.19) |
| KID-L | 0.61(0.24) | 0.38(0.08) | 0.34(0.21) | 0.32(0.12) |
| TUMOR | 10.40(1.47) | 0.40(0.09) | — | — |
| MUSCLE | 0.32(0.07) | 0.27(0.02) | 0.32(0.12) | 0.15(0.03) |

*Averages (standard deviations in parenthesis)

The results from these studies indicate that the antibody conjugate localized only to the tumor, with an average of about 10% I.D./g. The free drug showed localization to the tumor of less than 0.5% I.D./g. and a small (1-2.5% I.D./g) uptake to the spleen.

What is claimed is:
1. Idarubicin-13-adipic dihydrazide hydrazone.
2. 3'N,N-Dimethyladriamycin—13 adipic dihydrazide hydrazone.

* * * * *